United States Patent [19]

Meguro et al.

[11] Patent Number: 4,892,875
[45] Date of Patent: Jan. 9, 1990

[54] SUBSTITUTED HETEROCYCLYLALKYL ESTERS OF 1,4-DIHYDROPYRIDINE-3,5-DICARBOXYLIC ACIDS

[75] Inventors: Kanji Meguro, Nishinomiya; Akinobu Nagaoka, Kawanishi, both of Japan

[73] Assignee: Takeda Chemical Industries, Ltd., Osaka, Japan

[21] Appl. No.: 693,196

[22] Filed: Jan. 22, 1985

Related U.S. Application Data

[63] Continuation of Ser. No. 488,663, Apr. 26, 1983, abandoned.

[30] Foreign Application Priority Data

May 10, 1982 [WO] PCT Int'l Appl. .................. PCT/JP/82/00159
Jan. 11, 1983 [WO] PCT Int'l Appl. ... PCT/JP83/00008

[51] Int. Cl.$^4$ .................. A61K 31/495; C07D 401/12
[52] U.S. Cl. ..................................... 514/253; 514/218;
514/252; 514/254; 514/333; 514/338; 514/341;
540/575; 544/360; 544/364; 544/365; 546/256;
546/271; 546/278
[58] Field of Search ........................ 544/365, 360, 364;
546/256, 271, 278; 260/244.4; 424/244, 250, 263; 540/575; 514/218, 252, 253, 333, 338, 341

[56] References Cited

U.S. PATENT DOCUMENTS

| 3,472,853 | 10/1969 | Archer | 544/394 |
| 3,905,970 | 9/1975 | Bossert et al. | 544/360 |
| 3,959,292 | 5/1976 | Meyer et al. | 544/365 |
| 4,380,547 | 4/1983 | Materne | 546/279 |

FOREIGN PATENT DOCUMENTS

| 052300 | 10/1981 | European Pat. Off. | 544/360 |
| 063747 | 4/1982 | European Pat. Off. | 544/360 |
| 60674 | 9/1982 | European Pat. Off. | 544/360 |
| 80220 | 6/1983 | European Pat. Off. | 546/279 |

OTHER PUBLICATIONS

Yoshitomi Pharm, Derwent Abstract, 92122 (11-4-81).

Primary Examiner—Glennon H. Hollrah
Assistant Examiner—James H. Turnipseed
Attorney, Agent, or Firm—Wegner & Bretschneider

[57] ABSTRACT

Dihydropyridine derivatives and acid addition salts thereof which are of use as prophylactic or/and therapeutic drugs for cardiovascular diseases, said dihydropyridine derivatives having the formula

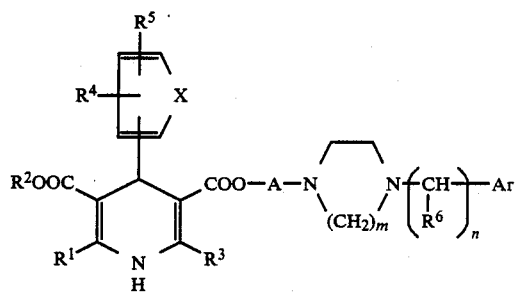

wherein $R^1$, $R^2$ and $R^3$ are the same or different and each is alkyl, cycloalkyl, cycloalkylalkyl or alkoxyalkyl; $R^4$ and $R^5$ are the same or different and each is hydrogen, halogen, nitro, trifluoromethyl, alkyl, cycloalkyl, alkoxy, cyano, alkoxycarbonyl or alkylthio; $R^6$ is hydrogen, alkyl, cycloalkyl, aralkyl, aryl or a pyridyl; X is oxygen, sulfur, vinylene, azomethine or a group of the formula

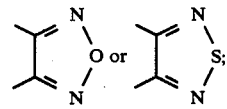

A is alkylene; Ar is aryl or a pyridyl; m is an integer of 1 to 3; n is an integer of 0 to 2.

15 Claims, No Drawings

SUBSTITUTED HETEROCYCLYLALKYL ESTERS OF 1,4-DIHYDROPYRIDINE-3,5-DICARBOXYLIC ACIDS

This application is a continuation of Ser. No. 488,663, filed Apr. 26, 1983 now abandoned.

It is known that several dihydropyridines having a skeletal structure similar to that of compounds of this invention have coronary artery dilating and antihypertensive activities.

However, a broad field of synthetic chemistry remains yet to be explored for dihydropyridine derivatives and it is true, even the more, of pharmacologic investigations of such compounds.

This invention relates to novel dihydropyridine derivatives having desirable pharmacological activities.

More particularly, this invention provides dihydropyridine derivatives of formula (I)

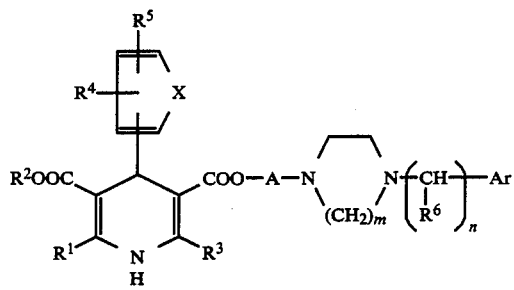

[wherein $R^1$, $R^2$ and $R^3$ are the same or different and each is alkyl, cycloalkyl or alkoxyalkyl; $R^4$ and $R^5$ are the same or different and each is hydrogen, halogen, nitro, trifluoromethyl, alkyl, cycloalkyl, alkoxy, cyano, alkoxycarbonyl or alkylthio; $R^6$ is hydrogen, alkyl, cycloalkyl, aralkyl, aryl or a pyridyl; X is oxygen, sulfur, vinylene, azomethine or a group of the formula

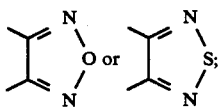

A is alkylene; Ar is aryl or a pyridyl; m is an integer of 1 to 3; n is an integer of 0 to 2]and acid addition salts thereof, which derivatives and acid addition salts have strong and long-lasting antihypertensive, peripheral vasodilating, coronary artery dilating, cerebral vasodilating, renal vasodilating and other activities and, therefore, are of value as medicines.

Referring to the above formula, the alkyls designated by $R^1$, $R^2$ and $R^3$ are preferably lower ($C_{1-6}$) alkyls which may be either straight-chain or branched, such as methyl, ethyl, propyl, isopropyl, butyl, isobutyl, sec-butyl, t-butyl, pentyl, isopentyl, neopentyl, hexyl, etc., although $C_{1-4}$ alkyls are particularly desirable. These alkyls may each terminate with a further lower ($C_{3-6}$) cycloalkyl group (e.g. cyclopropylmethyl, cyclobutylethyl, cyclopentylmethyl). The cycloalkyl is preferably lower ($C_3-C_6$) cycloalkyl, such as cyclopropyl, cyclobutyl, cyclopentyl, cyclohexyl, etc. The alkoxyalkyl preferably has a total of 3 to 7 carbon atoms and may for example be methoxyethyl, ethoxyethyl, propoxyethyl, isopropoxyethyl, butoxyethyl, methoxypropyl, 2-methoxy-1-methylethyl, 2-ethoxy-1-methylethyl or the like.

The substituents designated by $R^4$ and $R^5$ may be the same or different, and be present in any optional position of the ring, although they are preferably located in 2- or/and 3-position with respect to the site of attachement to the dihydropyridine ring. The halogen as an example of such substituents may be fluorine, chlorine, bromine or iodine and is preferably fluorine or chlorine. The alkyl and cycloalkyl are preferably those mentioned for $R^1$ through $R^3$. The alkoxy and alkylthio are preferably those containing lower ($C_{1-3}$) alkyls, thus being exemplified by methoxy, ethoxy, propoxy and isopropoxy and by methylthio, ethylthio, propylthio and isopropylthio, respectively. Examples of said alkoxycarbonyl include those containing 2 to 4 carbon atoms, such as methoxycarbonyl, ethoxycarbonyl, etc.

The alkyl and cycloalkyl, as designated by $R^6$, may be those mentioned for $R^1$ through $R^3$. The aralkyl may be phenyl $C_{1-3}$alkyls such as benzyl, α-phenylethyl, β-phenylethyl, γ-phenylpropyl, etc., and the aryl may be phenyl or naphthyl. The benzene ring thereof may have the same or different substituents in optional positions. Such substituents on the benzene ring may for example be those mentioned for $R^4$ and $R^5$. The pyridyl may be 2-pyridyl, 3-pyridyl or 4-pyridyl, which may have the substituents mentioned for $R^4$ and $R^5$.

The alkylene designated by A is preferably a group of $C_{2-4}$ which may be straight-chain or branched, thus being exemplified by ethylene, trimethylene, propylene, tetramethylene, 1,2-dimethylethylene, etc.

The aryl and pyridyl designated by Ar may be those mentioned for $R^6$ and may have substituents similar to those mentioned. When $R^6$ is aryl or pyridyl, Ar may represent either the same aryl or pyridyl or different aryl or pyridyl group.

Referring to m which is an integer of 1 to 3 and n which is an integer of 0 to 2, the case in which n is 0 is that the nitrogen atom is directly attached to Ar.

The ring

which is a substituent at the 4-position of the dihydropyridine ring is a benzene ring when X is vinylene (—CH=CH—) but means a heterocyclic ring or a fused heterocyclic ring in other cases. Thus, when X is oxygen or sulfur, the ring is furan or thiophene; when X is azomethine (—CH=N—), the ring is pyridine; when X is

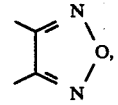

the ring is 2,1,3-benzoxadiazole; and when X is

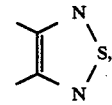

the ring is benzothiadiazole. These heterocyclic rings or fused heterocyclic rings may be attached in any optional position thereof to the 4-position of the dihydropyridine ring but the cases in which X is adjacent to the site of attachment to the dihydropyridine ring are particularly desirable. Preferred examples of such heterocyclic or fused heterocyclic groups are 2-furyl, 2-thienyl, 2-pyridyl, 3-pyridyl, 2,1,3-benzoxadiazol-4-yl, 2,1,3-benzothiadiazol-4-yl, etc.

In the production of the dihydropyridine derivatives of formula (I) of this invention, (I)

the starting material corresponding to a fragment which can constitute the dihydropyridine derivative (I) may be subjected to dehydration and cyclization reaction with the remaining fragment(s) in a manner conventional per se.

The following are typical examples of the production of the compound (I).

Production Process A (II)   (III)

(IV)

Production Process B

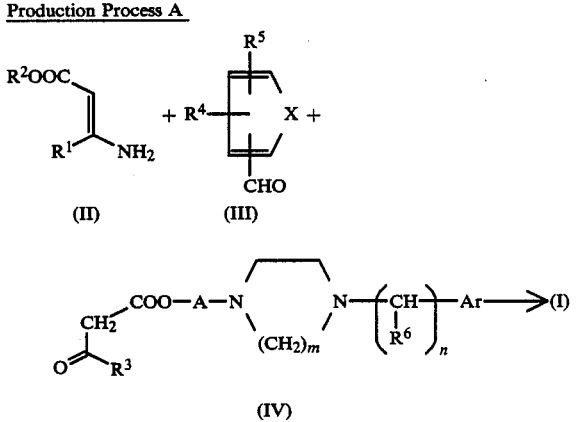

(V)   (III)

(VI)

Production Process C

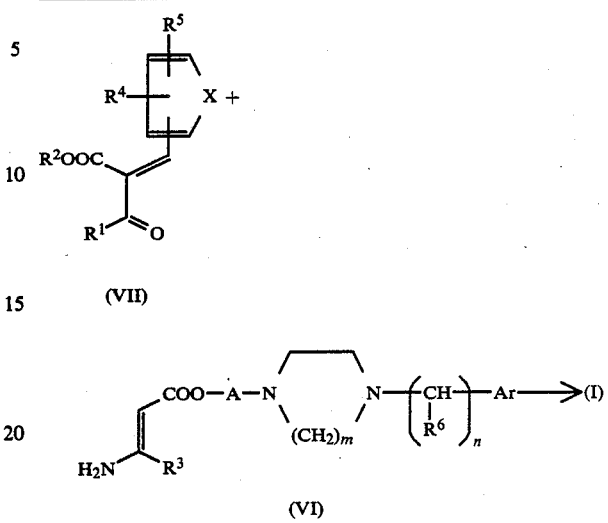

(VII)

(VI)

Production Process D (VII)

(IV)

Production Process E (II)

(VIII)

Production Process F

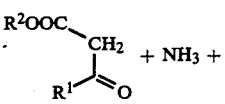

(V)

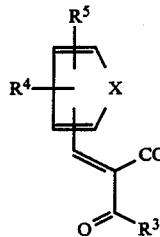

(VII)

In the above formulas, all symbols have the same meanings as defined hereinbefore.

Each of these production processes will be described in detail below.

PRODUCTION PROCESS A

In this process, compounds (II), (III) and (IV) are reacted in a suitable solvent. This reaction is generally conducted at a temperature of about 20° C. to about 160° C., preferably at about 50° C. to about 130° C., and most conveniently at the boiling point of the solvent used. The solvent may be any solvent that is inert to the reaction. Examples of the solvent include alkanols such as methanol, ethanol, propanol, isopropyl alcohol, butanol, sec-butanol, etc., ethers such as ethyl ether, dioxane, tetrahydrofuran, ethylene glycol monomethyl ether, ethylene glycol dimethyl ether, etc., acetic acid, pyridine, N,N-dimethylformamide, dimethyl sulfoxide, acetonitrile, etc. The reaction goes to completion generally in 0.5 to 15 hours. The proportions of (II), (III) and (IV) are such that to each mole of any one of these compounds, 1 to 1.5 moles each of the other two compounds are employed. The starting compound (II) is either a known compound or can be produced by a known production process [e.g. J. Am. Chem. Soc. 67, 1017 (1945)]. The compound (IV) can be produced by the following exemplary process.

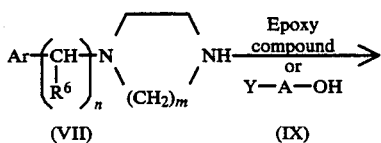

(1)

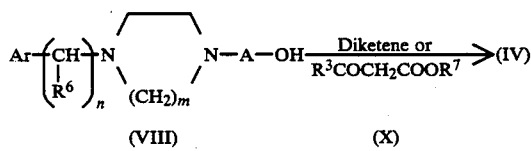

Wherein $R^7$ is lower alkyl; Y is halogen; and all other symbols have the same meanings as defined hereinbefore.

In the first place (VII) is reacted with an epoxy compound having an alkylene group corresponding to A moiety (e.g. ethylene oxide, propylene oxide) or a halohydrin of formula (IX) to synthesize (VIII). The reaction of (VII) with said epoxy compound is generally conducted in an appropriate solvent (e.g. water, methanol, ethanol, dioxane, tetrahydrofuran, etc.) at 20° C. to 100° C. The reaction of (VII) with (IX) to give (VIII) is preferably conducted in the presence of a base such as sodium carbonate, potassium carbonate, etc. As the solvent, acetone, methyl ethyl ketone, N,N-dimethylformamide, etc. may also be employed as well as those mentioned above, and the reaction may also be conducted at 20° C. to 100° C. The halogen Y in formula (IX) is chlorine, bromine or iodine, and when Y is chlorine or bromine, the reaction may be carried out in the presence of about 0.1 to 1 molar equivalents of sodium iodide, potassium iodide or the like per mole of (VII) so as to accelerate the reaction.

The compound (VIII) is then reacted with diketene or a β-keto ester of formula (X) to synthesize (IV). The reaction of (VIII) with diketene is generally carried out by heating a mixture of the reactants at a temperature of about 40° C. to about 130° C. This reaction may be conducted in the presence of a solvent inert to the reaction. This reaction gives rise to a compound (IV) in which $R^3$ is methyl. Alternatively, (IV) may be produced by reacting (VIII) with a β-keto ester of formula (X). This reaction may be conducted in the presence of a base such as sodium methoxide, sodium ethoxide, potassium t-butoxide, sodium hydride, sodium amide, sodium metal or the like, in the presence or absence of a suitable inert solvent, at a temperature of about 20° C. to about 100° C.

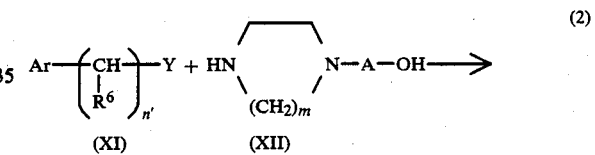

(XI)        (XII)

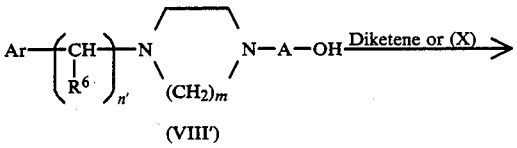

(VIII')

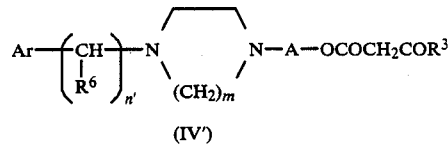

(IV')

Wherein n' is an integer of 1 to 2; all other symbols have the same meanings as defined hereinbefore.

This reaction process yields a starting compound (IV) in which n≠0, i.e. a compound of formula (IV'). The reaction of (XI) with (XII) and the reaction of (VIII') with diketene or (X) may be conducted under the same conditions as the above-mentioned reaction (1) of (VII) with (IX) and the reaction (1) of (VIII) with diketene or (X), respectively.

PRODUCTION PROCESS B

This production process may be conducted substantially under the same conditions as Production Process A. The starting compound (VI) can be synthesized by permitting ammonia to react with the starting compound (IV) used in Production Process A. Thus, (IV) is dissolved in a suitable solvent (e.g. methanol, ethanol, ethyl ether, dioxane, tetrahydrofuran) and an excess of ammonia gas is bubbled into the reaction mixture at about 0° C. to about 60° C. Or, a solution of ammonia in the above-mentioned solvent is added and the reaction is conducted in a closed vessel at about 0° C. to about 60° C. In either manner, (VI) can be easily synthesized.

PRODUCTION PROCESS C

In this production process, benzylidene β-keto ester (VII) is reacted with compound (VI) to give the object compound (I). The reaction conditions of this process are also substantially identical with those of Production Process A. Thus, each mole of compound (VII) is reacted with 0.8 to 1.5 moles of (VI). The starting benzylidene β-keto ester (VII) is either a known compound or can be prepared from the aldehyde (III) and β-keto ester (V) by the convention procedure [e.g. Organic Reactions 15, 204–599 (1967)].

PRODUCTION PROCESS D

In this production process, ammonia and compound (IV) are simultaneously reacted with (VII) instead of (VI) alone in Production Process C. It appears that in this system, ammonia reacts with (IV) in the first place to give (VI) which then reacts with (VII). Therefore, this process may be conducted substantially under the same conditions as Production Process C. The molar proportion of (IV) relative to each mole of (VII) is generally 0.8 to 1.5 moles and that of ammonia is 1 to 5 moles on the same basis.

PRODUCTION PROCESS E

In this process, (II) and (VIII) are reacted substantially under the same conditions as in Production Process C. Like (VII), the starting benzylidene β-keto ester (VIII) can be synthesized by reacting the aldehyde (III) with the β-keto ester [e.g. Organic Reactions 15, 204–599 (1967)]. Generally this reaction is conducted using 0.8 to 1.5 moles of (II) to each mole of (VIII).

PRODUCTION PROCESS F

In this process, ammonia and (V) are simultaneously reacted with (VIII) instead of (II) alone in Production Process E. It appears that in this process, ammonia reacts with (V) in the first place to give (II) which then reacts with (VIII). Therefore, this reaction may be conducted substantially under the same conditions as in Production Process E. The molar proportion of (V) relative to each mole of (VIII) is generally 0.8 to 1.5 moles and that of ammonia is 1 to 5 moles on the same basis.

The novel dihydropyridine derivative (I) produced in the manners described above can be isolated in a desired purity by the per se conventional separation and purification procedures such as concentration, extraction, chromatography, reprecipitation, recrystallization, etc. Since (I) contains a basic group, it can be converted to an acid addition salt by the known procedure. The salt is preferably a pharmaceutically acceptable non-toxic salt such as salts with mineral acids (hydrochloride, hydrobromide, phosphate, sulfate, etc.) and salts with organic acids (acetate, succinate, maleate, fumarate, malate, tartarate, methanesulfonate, etc.).

The compound (I) and its salt according to this invention have low toxicity and display strong and long-lasting antihypertensive, peripheral vasodilating, coronary artery dilating, cerebral vasodilating, renal vasodilating and other activities in mammalian animals (e.g. mouse, rat, rabbit, dog, cat, man), and are of value in the prevention and treatment of cardiovascular diseases such as hypertension, ischemic heart disease (angina pectoris, myocardial infarction, etc.), cerebral and peripheral circulatory disorder (cerebral infarction, transient cerebral ischemic attack, renal artery stenosis, etc.), for instance. The present compound is very useful in that it is superior to the known dihydropyridine derivatives (e.g. nifedipine, nicardipine) in the intensity and duration of action and has the distinct property of dilating the renal blood vessels to increase the renal blood flow which is not found in the known compounds. When used as a prophylactic or therapeutic drug for hypertension, for instance, the compound of this invention produces a stable antihypertensive effect in a less frequent administration regimen (e.g. 1 to 2 doses per day). The increase of renal blood flow due to its renal vessel dilating activity promotes excretion of excess sodium and suppresses retention of sodium in the body. That is to say, the retention of sodium in the body due to an excessive intake of sodium chloride and the depressed sodium excreting function in hypertensive patients are improved, leading to an excellent antihypertensive effect. Moreover, since it is known that excessive sodium chloride intakes not only cause hypertension but also provoke onset of cerebral apoplexy, a mild diuretic action via an increase of renal blood flow appears to be useful for the prevention of hypertensive vascular disorders such as cerebral apoplexy. Furthermore, a decreased renal blood flow promotes release of renin (an enzyme which produces angiotensin which is a vasopressor substance) from the kidney. Therefore, the renal hemodynamics improving action of the compounds of this invention may be pressumed to supress secretion of renin and the compound (I) and salt thereof are of use as antihypertensive drugs.

In the use of the compound (I) or its salt, it can be administered orally or otherwise in such dosage forms as powders, granules, tablets, capsules, injections, etc. which may be prepared by mixing the compound (I) or salt thereof with a pharmaceutically acceptable carrier, excipient or diluent. The dosage should vary with such factors as the route of administration, the condition, body weight and age of the patient, etc. but for oral administration to an adult patient with hypertension, for instance, 0.05 to 20 mg/kg body weight/day or preferably 0.1 to 4 mg/kg body weight/day is administered divided into 1 to several times a day.

The following are the results of pharmacological tests indicating the utility of compounds (I) according to this invention and the acute toxicity test data.

1. Antihypertensive action

[Procedure]

Male spontaneously hypertensive rats aged 10 to 11 weeks were used (in groups of 3 to 6 individuals). The blood pressures were about 200 mmHg at the systolic blood pressures. To determine the blood pressure, an automatic blood pressure meter of Ueda Medical Co., Ltd. (USM-105R) was used to measure the systolic blood pressure in the caudal artery of each rat.

Each test compound was suspended in a 5% solution of gum arabic and orally administered. The dosage was 10 mg/kg for all compounds. Animals in a control group was given the above solution of gum arabic only. Blood pressure measurements were made 1, 5, 8 and 24 hours after administration of each test compound.

[Results]

The antihypertensive effects (blood pressure after medication minus blood pressure before medication) of compounds of this invention are shown in Table 1.

TABLE 1

| | Antihypertensive Effects | | |
| --- | --- | --- | --- |
| | Change in blood pressure (mmHg) | | Duration of |
| Compound (Example No.) | 1 hr. after treatment | 5 hrs. after treatment | antihypertensive effect (in hrs.) |
| Control group (given gum arabic) | +2 | −2 | 0 |
| 1 | −89* | −91* | >24 |
| 2 | −99* | −101* | 8-24 |
| 6 | −30* | −33* | 8-24 |
| 7 | −59* | −79* | >24 |
| 8 | −96* | −98* | >24 |
| 9 | −96* | −98* | >24 |
| 10 | −88* | −57* | 8-24 |
| 12 | −85* | −87* | >24 |
| 13 | −34* | −31* | 8-24 |
| 15 | −38* | −18* | 5-8 |
| 16 | −51* | −45* | 8-24 |
| 17 | −77* | −46* | 8-24 |
| 18 | −68* | −43* | 8-24 |
| 22 | −97* | −83* | 8-24 |
| 23 | −59* | −66* | 8-24 |
| 24 | −49* | −30* | ca. 8 |
| 28 | −93* | −75* | 8-24 |
| 30 | −48* | −31* | 8-24 |
| 31 | −77* | −77* | 8-24 |
| 32 | −46* | −48* | 8-24 |
| 33 | −51* | −60* | 8-24 |
| 37 | −63* | −30* | ca. 8 |
| 38 | −50* | −42* | 8-24 |
| 41 | −55* | −67* | ca. 24 |
| 42 | −25* | −35* | 8-24 |
| 43 | −54* | −44* | 8-24 |
| 44 | −44* | −22* | 8-24 |
| 45 | −57* | −42* | 8-24 |
| 46 | −44* | −43* | 8-24 |
| 50 | −58* | −37* | 8-24 |
| 51 | −69* | −54* | 8-24 |
| 52 | −54* | −14* | ca. 8 |
| 53 | −60* | −34* | ca. 8 |
| 57 | −85* | −69* | 8-24 |
| 58 | −27* | −39* | 8-24 |
| 60 | −98* | −90* | 8-24 |
| Nifedipine[1] | −45* | −3 | <5 |
| Nicardipine.HCl[2] | −38* | +2 | <5 |

*P < 0.05 (compared with control group)

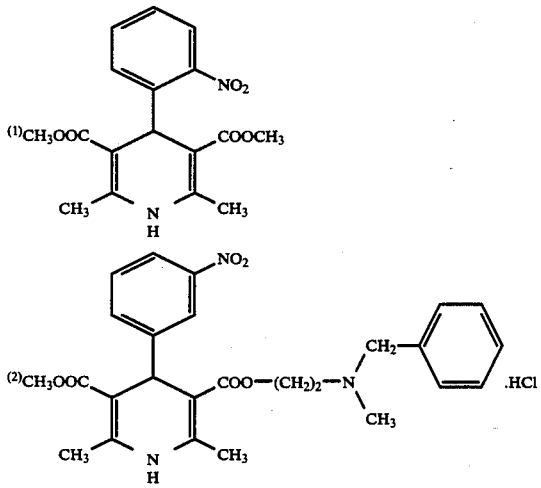

It will be apparent from Table 1 that compounds of this invention are at least equivalent or superior to the known dihydropyridine derivatives (nifedipine and nicardipine) in the intensity of action and show much more long-lasting action as compound with the latter compounds.

2. Renal blood flow increasing effect (renal circulation improving effect)

[Procedure]

Male spontaneously hypertensive rats aged 10 to 11 weeks (3 to 6 animals per group) were anesthetized with pentobarbital and used. After laparotomy, an electromagnetic flowmeter probe (Narco) was fitted to the left renal artery and the renal blood flow was continuously recorded on a polygraph (Sanei Sokki K.K.). The renal blood flows before medication were about 6.5 ml per min.

Each test compound was dissolved in polyethylene glycol 400 to prepare a stock solution. This stock solution was diluted five-fold with physiological saline and the dilution was intravenously administered to rats in a volume of 0.5 ml/kg body weight. The dosage was 0.01 mg/kg for all test compounds. The renal blood flow was measured over a period of 40 minutes following the medication.

[Results]

The effects of compounds of this invention on renal blood flow are shown in Table 2. The values shown are:

$$\frac{\left(\begin{array}{c}\text{Renal blood flow}\\\text{after medication}\end{array}\right) - \left(\begin{array}{c}\text{Renal blood flow}\\\text{before medication}\end{array}\right)}{\text{Renal blood flow before medication}} \times 100\ (\%)$$

TABLE 2

| | Renal blood flow increasing effects | | |
| --- | --- | --- | --- |
| | Change in renal blood flow (%) | | |
| Compound (Example No.) | 1 Minute after medication | 20 Minutes after medication | 40 Minutes after medication |
| Control group (solvent vehicle only) | 2.4 | 2.9 | 3.4 |
| 1 | 10.4* | 13.4* | 12.8* |
| 6 | 4.5* | 7.5* | 6.0* |
| 8 | 5.7* | 6.4* | 9.7* |
| 10 | 6.9* | 8.3* | 6.8* |
| 15 | 4.2* | 4.2* | 2.9* |
| 18 | 8.8* | 4.2* | 5.0* |
| 22 | 7.5* | 7.8* | 9.6* |
| 23 | 6.7* | 9.7* | 10.9* |
| 31 | 3.3 | 4.3* | 1.8 |
| 37 | 8.5* | 10.8* | 11.3* |
| Nifedipine | 3.0 | 3.1 | 2.2 |
| Nicardipine.HCl | −15.0* | −1.9 | 0.3 |

*: P < 0.05 (compared with control group)

3. Acute toxicity

[Procedure]

2-(4-Benzhydryl-1-piperazinyl)ethyl methyl 2,6-dimethyl-4-(3-nitrophenyl)-1,4-dihydropyridine-3,5-dicarboxylate dihydrochloride was suspended in a 5% solution of gum arabic and orally administered to male and female Wistar rats aged 5 weeks (body weight 105 to 139 g) in a dose of 62.5, 125, 250, 500 and 1000 mg/kg (in groups of 4 to 8) and each animal so treated was observed over a period of 7 days.

[Results]

The acute toxicity test data are shown in Table 3.

TABLE 3

| Acute toxicity (LD50, mg/kg) | | |
|---|---|---|
| Rat | ♂ | 250 < LD50 < 500 |
| | ♀ | 250 < LD50 < 500 |

The examples, formulation examples and reference examples are described in the following to illustrate this invention more specifically.

The melting point values shown in the following examples were measured by the hot plate method and are uncorrected.

EXAMPLE 1

A mixture of m-nitrobenzaldehyde (2.66 g), 2-(4-benzhydryl-1-piperazinyl)ethyl acetoacetate (6.09 g), methyl 3-aminocrotonate (2.03 g) and isopropyl alcohol (25 ml) was refluxed for 6 hours. The solvent was distilled off and the residue was purified by chromatography [silica gel: 250 g; eluent: hexane-ethyl acetate (1:1)]. The resulting oily substance was dissolved in a small amount of isopropyl ether and under ice-cooling and stirring, hexane was added to give a powder (7.35 g, 75.2%) of 2-(4-benzyhydryl-1-piperazinyl)ethyl methyl 2,6-dimethyl-4-(3-nitrophenyl)-1,4-dihydropyridine-3,5-dicarboxylate. A portion of the powder was recrystallized from isopropyl ether-hexane to give light yellow crystals, m.p. 102°–104° C. NMR (CDCl$_3$)δ: 2.26–2.49(8H,m), 2.33(6H,s), 2.57(2H,t,J=6), 3.60(3H,s), 4.15(2H,t,J=6), 4.18(1H,s), 5.08(1H,s), 5.77(1H,s), 7.11–8.12(14H,m).

Elemental analysis:
Calcd. for C$_{35}$H$_{38}$N$_4$O$_6$:
C, 68.83; H, 6.27; N, 9.17.
Found: C, 68.97; H, 6.27; N, 9.05.

The above free base (3.90 g) was dissolved in dichloromethane (10 ml) and a solution of hydrogen chloride in dioxane was added in slight excess. After ice-cooling, a few drops of water was added and the mixture was stirred under ice-cooling. The resulting crystalline precipitate was collected by filtration and washed with ethyl ether to give 2-(4-benzhydryl-1-piperazinyl)ethyl methyl 2,6-dimethyl-4-(3-nitrophenyl)-1,4-dihydropyridine-3,5-dicarboxylate dihydrochloride in the form of monohydrate, yield 4.23 g (94.4%). This product was dissolved in dichloromethane containing a small amount of methanol. The solvent was then distilled off and the residue was dissolved in ethyl acetate and after addition of water, the mixture was allowed to stand with ice-cooling. This recrystallization procedure gave light yellow crystals, m.p. 167°–170° C.

Elemental analysis:
Calcd. for C$_{35}$H$_{38}$N$_4$O$_6$.2HCl.H$_2$O:
C, 59.90; H, 6.03; N, 7.99.
Found: C, 60.06; H, 5.97; N, 7.84.

EXAMPLE 2

A mixture of m-nitrobenzaldehyde, 2-(4-benzhydryl-1-piperazinyl)ethyl acetoacetate and ethyl 3-aminocrotonate was reacted in isopropyl alcohol in the same manner as Example 1 to give 2-(4-benzhydryl-1-piperazinyl)ethyl ethyl 2,6-dimethyl-4-(3-nitrophenyl)-1,4-dihydropyridine-3,5-dicarboxylate as a light yellow powder, m.p. 80°–82° C. (sintering). Yield 48.3%. IR(Nujol)cm$^{-1}$: 3320, 1695, 1680. NMR(CDCl$_3$) δ: 1.18(3H,t,J=6,—CH$_2$CH$_3$), 2.33(6H,s,

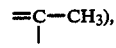

4.08(2H,q,J=6, —CH$_2$CH$_3$), 4.15(2H,t,J=6, —COOCH$_2$CH$_2$—), 4.18(1H,s,>N—CH<), 5.08(1H,s,C$_{(4)}$—H), 5.79(1H,s,NH).

Elemental analysis:
Calcd. for C$_{36}$H$_{40}$N$_4$O$_6$:
C, 69.21; H, 6.45; N, 8.97.
Found: C, 68.82; H, 6.63; N, 8.72.

EXAMPLE 3

A mixture of o-nitrobenzaldehyde, 2-(4-benzhydryl-1-piperazinyl)ethyl acetoacetate and methyl 3-aminocrotonate was worked up in isopropyl alcohol in the same manner as Example 1 and the product was further treated with methanolic hydrogen chloride to give 2-(4-benzhydryl-1-piperazinyl)ethyl methyl 2,6-dimethyl-4-(2-nitrophenyl)-1,4-dihydropyridine-3,5-dicarboxylate dihydrochloride monohydrate as light yellow crystals, m.p. 162°–164° C. Yield 11.4%.

Elemental analysis:
Calcd. for C$_{35}$H$_{38}$N$_4$O$_6$.2HCl.H$_2$O:
C, 59.90; H, 6.03; N, 7.99.
Found: C, 60.12; H, 6.15; N, 7.89.

EXAMPLE 4

A mixture of o-chlorobenzaldehyde, 2-(4-benzhydryl-1-piperazinyl)ethyl acetoacetate and methyl 3-aminocrotonate was worked up in isopropyl alcohol in the same manner as Example 1 to give 2-(4-benzhydryl-1-piperazinyl)ethyl methyl 4-(2-chlorophenyl)-2,6-dimethyl--1,4-dihydropyridine-3,5-dicarboxylate as a light yellow powder, m.p. 81°–83° C. (sintering). Yield (30.8%). IR(Nujol)cm$^{-1}$: 3320, 1680. NMR(CDCl$_3$)δ: 2.26(6H,s,

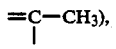

3.56(3H,s,COOCH$_3$), 4.12(2H,t,J=6,—COOCH$_2$CH$_2$—), 4.17(1H,s, >N—CH<), 5.36(1H,s,C$_{(4)}$—H), 5.63(1H,s,NH).

Elemental analysis:
Calcd. for C$_{35}$H$_{38}$ClN$_3$O$_4$:
C, 70.04; H, 6.38; N, 7.00.
Found: C, 69.84; H, 6.45; N, 6.83.

EXAMPLE 5

A mixture of o-chlorobenzaldehyde, 2-(4-benzhydryl-1-piperazinyl)ethyl acetoacetate and ethyl 3-aminocrotonate was worked up in isopropyl alcohol in the same manner as Example 1 to give 2-(4-benzhydryl-1-piperazinyl)ethyl ethyl 4-(2-chlorophenyl)-2,6-dimethyl-1,4-dihydropyridine-3,5-dicarboxylate as a light yellow powder, m.p. 76°–78° C. (sintering). Yield 34.7%. IR(Nujol) cm$^{-1}$: 3320, 1690, 1680. NMR (CDCl$_3$)δ:1.17(3H,t,J=7, —CH$_2$CH$_3$), 2.20(6H, s,

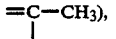

4.20(1H,s,>N—CH<), 5.40(1H,s,C(4)—H), 6.37(1H,s,NH).

Elemental analysis:
Calcd. for $C_{36}H_{40}ClN_3O_4$: C, 70.40; H, 6.56; N, 6.84.
Found: C, 70.12; H, 6.77; N, 6.57.

EXAMPLE 6

A mixture of 2,3-dichlorobenzaldehyde, 2-(4-benzhydryl-1-piperazinyl)ethyl acetoacetate and methyl 3-aminocrotonate was worked up in isopropyl alcohol in the same manner as Example 1 to give 2-(4-benzhydryl-1-piperazinyl)ethyl methyl 4-(2,3-dichlorophenyl)-2,6-dimethyl-1,4-dihydropyridine-3,5-dicarboxylate as a light yellow powder, m.p. 84°–88° C. (sintering). Yield 31.6%. IR(Nujol)cm$^{-1}$: 3320, 1730, 1690. NMR(CDCl$_3$) δ: 2.28(6H, s,

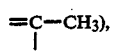

3.58(3H,s,COOCH$_3$), 4.15(2H,t,J=6,—COOC$\underline{H_2}$C-$\underline{H_2}$—), 4.19(1H,s,>N—CH<), 5.45(1H,s,C(4)—H), 5.61(1H,s,NH).

Elemental analysis:
Calcd. for $C_{35}H_{37}Cl_2N_3O_4$: C, 66.24; H, 5.88; N, 6.62.
Found: C, 66.38; H, 5.99; N, 6.37.

EXAMPLE 7

A mixture of 2,3-dichlorobenzaldehyde, 2-(4-benzhydryl-1-piperazinyl)ethyl acetoacetate and ethyl 3-aminocrotonate was worked up in isopropyl alcohol in the same manner as Example 1 to give 2-(4-benzhydryl-1-piperazinyl)ethyl ethyl 4-(2,3-dichlorophenyl)-2,6-dimethyl-1,4-dihydropyridine-3,5-dicarboxylate as a light yellow powder, m.p. 87°–89° C. (sintering). Yield 30.7%. IR(Nujol)cm$^{-1}$: 3335, 1695, 1680. NMR(CDCl$_3$) δ: 1.15(3H, t,J=7,—CH$_2$C$\underline{H_3}$), 3.25(6H,s,

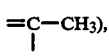

4.16(1H,s,>N—CH<), 5.41(1H,s,C(4)—H), 5.96(1H,s,NH).

Elemental analysis:
Calcd. for $C_{36}H_{39}Cl_2N_3O_4$: C, 66.66; H, 6.06; N, 6.48.
Found: C, 66.32; H, 5.97; N, 6.27.

EXAMPLE 8

A mixture of m-nitrobenzaldehyde, 2-[4-(4,4'-difluorobenzhydryl)-1-piperazinyl]ethyl acetoacetate and methyl 3-aminocrotonate was worked up in isopropyl alcohol in the same manner as Example 1 to give 2-[4-(4,4'-difluorobenzhydryl)-1-piperazinyl]ethyl methyl 2,6-dimethyl-4-(3-nitrophenyl)-1,4-dihydropyridine-3,5-dicarboxylate as a light yellow powder, m.p. 68°–72° C. (sintering). Yield 33.3%. This product was treated with methanolic hydrogen chloride to give colorless prisms of the dihydrochloride, m.p. 190°–193° C.

Elemental analysis:
Calcd. for $C_{35}H_{36}F_2N_4O_6\cdot2HCl$: C, 58.42; H, 5.32; N, 7.79.
Found: C, 58.25; H, 5.38; N, 7.44.

EXAMPLE 9

A mixture of m-nitrobenzaldehyde, 2-[4-(4,4'-dimethylbenzhydryl)-1-piperazinyl]ethyl acetoacetate and methyl 3-aminocrotonate was worked up in isopropyl alcohol in the same manner as Example 1 to give 2-[4-(4,4'-dimethylbenzhydryl)-1-piperazinyl]ethyl methyl 2,6-dimethyl-4-(3-nitrophenyl)-1,4-dihydropyridine-3,5-dicarboxylate as a light yellow powder, m.p. 83°–87° C. (sintering). Yield 53.1%. IR(Nujol)cm$^{-1}$: 3330, 1695, 1680(shoulder). NMR(CDCl$_3$) δ: 2.32(6H,s,

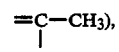

2.36(6H,s,

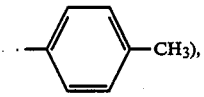

3.60(3H,s,COOCH$_3$), 4.10(1H,s,>N—CH<), 4.14(2H,t,J=6, —COOC$\underline{H_2}$CH$_2$—), 5.09(1H,s,C(4)—H), 5.84(1H,broad s, NH).

Elemental analysis:
Calcd. for $C_{37}H_{42}N_4O_6$: C, 69.57; H, 6.63; N, 8.77.
Found: C, 69.88; H, 6.82; N, 8.42.

EXAMPLE 10

A mixture of m-nitrobenzaldehyde, 2-[4-(4,4'-dimethoxybenzhydryl)-1-piperazinyl]ethylacetoacetate and methyl 3-aminocrotonate was worked up in isopropyl alcohol in the same manner as Example 1 to give 2-[4-(4,4'-dimethoxybenzhydryl)-1-piperazinyl]ethyl methyl 2,6-dimethyl-4-(3-nitrophenyl)-1,4-dihydropyridine-3,5-dicarboxylate as a light yellow powder, m.p. 76°–80° C. (sintering). Yield 39.3%. IR(Nujol)cm$^{-1}$: 3330, 1695, 1680(shoulder). NMR(CDCl$_3$) δ: 2.36(6H,s,

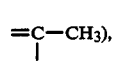

3.57(3H,s,—COOCH$_3$), 3.75(6H,s,OCH$_3$), 4.11(1H,s,>N—CH<), 4.15(2H,t,J=6, —COOC$\underline{H_2}$C-$\underline{H_2}$—), 5.08(1H,s,C(4)—H), 5.80(1H,broad s, NH).

Elemental analysis:
Calcd. for $C_{37}H_{42}N_4O_8$: C, 66.25; H, 6.31; N, 8.35.
Found: C, 66.22; H, 6.41; N, 8.12.

EXAMPLE 11

A mixture of o-nitrobenzaldehyde, 2-[4-(4,4'-difluorobenzhydryl)-1-piperazinyl]ethyl acetoacetate and methyl 3-aminocrotonate was worked up in isopropyl alcohol in the same manner as Example 1 to give 2-[4-(4,4'-difluorobenzhydryl)-1-piperazinyl]ethyl methyl 2,6-dimethyl-4-(2-nitrophenyl)-1,4-dihydropyridine-3,5-dicarboxylate as a light yellow powder, m.p. 90°–93° C. (sintering). Yield 21.3%. IR(KBr)cm$^{-1}$: 3350, 1695. NMR(CDCl$_3$) δ: 2.26(3H,s,

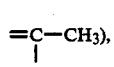

2.31(3H,s,

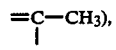

3.53(3H,s,COOCH₃), 4.0–4.3(3H,m,>N—CH<+—COOCH₂CH₂—), 5.72(1H,s,C₍₄₎—H), 5.77(1H,broad s, NH).

Elemental analysis:
Calcd. for $C_{35}H_{36}F_2N_4O_6$: C, 65.01; H, 5.61; N, 8.66.
Found: C, 65.40; H, 5.60; N, 8.39.

EXAMPLE 12

A mixture of m-nitrobenzaldehyde, 2-[4-(4,4′-dichlorobenzhydryl)-1-piperazinyl]ethyl acetoacetate and methyl 3-aminocrotonate was worked up in isopropyl alcohol in the same manner as Example 1 to give 2-[4-(4,4′-dichlorobenzhydryl)-1-piperazinyl]ethyl methyl 2,6-dimethyl-4-(3-nitrophenyl)-1,4-dihydropyridine-3,5-dicarboxylate as a light yellow powder, m.p. 83°–87° C. (sintering). Yield 57.8%. This product was further treated with ethanolic hydrogen chloride to give the dihydrochloride. Recrystallization from ethanol-ethyl ether gave light yellow prisms, m.p. 208°–211° C.

Elemental analysis:
Calcd. for $C_{35}H_{36}Cl_2N_4O_6 \cdot 2HCl$: C, 55.86; H, 5.09; N, 7.45.
Found: C, 56.00; H, 5.34; N, 7.38.

EXAMPLE 13

A mixture of 2,3-dichlorobenzaldehyde, 2-[4-(4,4′-difluorobenzhydryl)-1-piperazinyl]ethyl acetoacetate and methyl 3-aminocrotonate was worked up in isopropyl alcohol in the same manner as Example 1 to give 2-[4-(4,4′-difluorobenzhydryl)-1-piperazinyl]ethyl methyl 4-(2,3-dichlorophenyl)-2,6-dimethyl-1,4-dihydropyridine-3,5-dicarboxylate as a light yellow powder, m.p. 90°–93° C. (sintering). Yield 52.9%. IR(KBr)cm⁻¹: 3340, 1695. NMR(CDCl₃) δ: 2.28(6H,s,

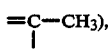

3.57(3H,s,COOCH₃), 4.12(2H,t,J=6,—COOCH₂CH₂—), 4.16(1H,s,>N—CH<), 5.42(1H,s,C₍₄₎—H), 5.70(1H,broad s, NH).

Elemental analysis:
Calcd. for $C_{35}H_{35}Cl_2F_2N_3O_4$: C, 62.69; H, 5.26; N, 6.27.
Found: C, 62.77; H, 5.50; N, 6.06.

EXAMPLE 14

A mixture of 2,3-dichlorobenzaldehyde, 2-[4-(4,4′-dichlorobenzhydryl)-1-piperazinyl]ethyl acetoacetate and methyl 3-aminocrotonate was worked up in isopropyl alcohol in the same manner as Example 1 to give 2-[4-(4,4′-dichlorobenzhydryl)-1-piperazinyl]ethyl methyl 4-(2,3-dichlorophenyl)-2,6-dimethyl-1,4-dihydropyridine-3,5-dicarboxylate as a light yellow powder, m.p. 104°–107° C. (sintering). Yield 43.2%. IR(KBr)cm⁻¹: 3340, 1695. NMR(CDCl₃) δ: 2.27(6H,s,

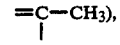

3.57(3H,s,COOCH₃), 4.12(2H,t,J=6,—COOCH₂CH₂—), 4.18(1H,s,>N—CH<), 5.43(1H,s,C₍₄₎—H), 5.70(1H,broad s, NH).

Elemental analysis:
Calcd. for $C_{35}H_{35}Cl_4N_3O_4$: C, 59.76; H, 5.01; N, 5.97.
Found: C, 59.52; H, 4.97; N, 5.75.

EXAMPLE 15

A mixture of m-nitrobenzaldehyde, 2-(4-benzhydrylhomopiperazin-1-yl)ethyl acetoacetate and methyl 3-aminocrotonate was worked up in isopropyl alcohol in the same manner as Example 1 to give 2-(4-benzhydrylhomopiperazin-1-yl)-ethyl methyl 2,6-dimethyl-4-(3-nitrophenyl)-1,4-dihydropyridine-3,5-dicarboxylate as a light yellow powder, m.p. 60°–63° C. (sintering). Yield 31.7%. IR(KBr)cm⁻¹: 3330, 1690. NMR(CDCl₃) δ: 2.33(6H,s,

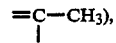

3.60(3H,s), 4.12(2H,t,J=6), 4.57(1H,s,>N—CH<), 5.10(1H,s,C₍₄₎—H), 5.92(1H,s,NH).

Elemental analysis:
Calcd. for $C_{36}H_{40}N_4O_6$: C, 69.21; H, 6.45; N, 8.97.
Found: C, 69.24; H, 6.51; N, 8.77.

EXAMPLE 16

A mixture of m-nitrobenzaldehyde, 2-[4-(4-fluorophenyl)-1-piperazinyl]ethyl acetoacetate and methyl 3-aminocrotonate was worked up in isopropyl alcohol in the same manner as Example 1, and the product obtained was further treated with a dioxane solution of hydrogen chloride to give 2-[4-(4-fluorophenyl)-1-piperazinyl]ethyl methyl 2,6-dimethyl-4-(3-nitrophenyl)-1,4-dihydropyridine-3,5-dicarboxylate hydrochloride as a light yellow powder, m.p. 108°–110° C. Yield 76.4%. NMR(DMSO-d₆) δ: 2.30(3H,s,

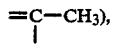

2.38(3H,s,

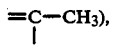

3.60(3H,s,COOCH₃), 4.48(2H,m,—COOCH₂CH₂—), 5.03(1H,s,C₍₄₎—H).

Elemental analysis:
Calcd. for $C_{28}H_{31}FN_4O_6 \cdot HCl \cdot H_2O$: C, 56.71; H, 5.78; N, 9.45.
Found: C, 56.78; H, 5.85; N, 9.35.

EXAMPLE 17

A mixture of m-nitrobenzaldehyde, 2-[4-(3-chlorophenyl)-1-piperazinyl]ethyl acetoacetate and methyl 3-aminocrotonate was worked up in isopropyl alcohol in the same manner as Example 1 to give 2-[4-(3-chlorophenyl)-1-piperazinyl]ethyl methyl 2,6-dimethyl-4-(3- nitrophenyl)-1,4-dihydropyridine-3,5-dicarboxylate as a light yellow powder, m.p. 65°-68° C. (sintering). Yield 29.0%. IR(Nujol)cm$^{-1}$: 3300. NMR(CDCl$_3$) δ: 2.34(3H,s,

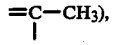

2.36(3H,s,

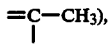

3.63(3H,s,COOCH$_3$), 4.21(2H,t,J=6,—COOC$\underline{H_2}$C-H$_2$—), 5.12(1H,s,C$_{(4)}$—H), 5.89(1H,s,NH).
Elemental analysis:
Calcd. for C$_{28}$H$_{31}$ClN$_4$O$_6$: C, 63.26; H, 6.22; N, 10.18.
Found: C, 63.33; H, 6.43; N, 9.83.

EXAMPLE 18

A mixture of m-nitrobenzaldehyde, 2-[4-(3-trifluoromethylphenyl)-1-piperazinyl]ethyl acetoacetate and methyl 3-aminocrotonate was worked up in isopropyl alcohol in the same manner as Example 1 to give methyl 2-[4-(3-trifluoromethylphenyl)-1-piperazinyl]ethyl 2,6-dimethyl-4-(3-nitrophenyl)-1,4-dihydropyridine-3,5-dicarboxylate as a light yellow powder, m.p. 95°-87° C. (sintering). Yield 82.7%. IR(Nujol)cm$^{-1}$: 3345, 1695, 1645. NMR(CDCl$_3$) δ: 2.34(6H,s,

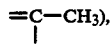

3.64(3H,s,COOCH$_3$), 4.21(2H,t,J=5.5,—COOC$\underline{H_2}$C-H$_2$—), 5.11(1H,s,C$_{(4)}$—H), 6.39(1H,s,NH).
Elemental analysis:
Calcd. for C$_{29}$H$_{31}$F$_3$N$_4$O$_6$: C, 59.18; H, 5.31; N, 9.52.
Found: C, 59.15; H, 5.53; N, 9.43.

EXAMPLE 19

A mixture of m-nitrobenzaldehyde, 2-[4-(2-methoxyphenyl)-1-piperazinyl]ethyl acetoacetate and methyl 3-aminocrotonate was worked up in isopropyl alcohol in the same manner as Example 1 to give 2-[4-(2-methoxyphenyl)-1-piperazinyl]-ethyl methyl 2,6-dimethyl-4-(3-nitrophenyl)-1,4-dihydropyridine-3,5-dicarboxylate as a light yellow powder, m.p. 58° C. (sintering). Yield 55.6%. NMR(CDCl$_3$) δ: 2.34(6H,s,

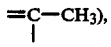

3.63(3H,s,OCH$_3$), 3.83(3H,s,OCH$_3$), 4.21(2H,t,J=6, —COOC$\underline{H_2}$CH$_2$—), 5.14(1H,s,C$_{(4)}$—H), 6.60(1H,s,NH).
Elemental analysis:
Calcd. for C$_{29}$H$_{34}$N$_4$O$_7$: C, 63.26; H, 6.22; N, 10.18.
Found: C, 63.33; H, 6.43; N, 9.83.

EXAMPLE 20

A mixture of m-nitrobenzaldehyde, 2-(4-benzyl-1-piperazinyl)ethyl acetoacetate and methyl 3-aminocrotonate was worked up in isopropyl alcohol in the same manner as Example 1 to give 2-(4-benzyl-1-piperazinyl)ethyl methyl 2,6-dimethyl-4-(3-nitrophenyl)-1,4-dihydropyridine-3,5-dicarboxylate as a light yellow powder, m.p. 106°-108° C. (sintering). Yield 86.0%. IR(Nujol)cm$^{-1}$: 3325. NMR(CDCl$_3$) δ: 2.33(6H,s,

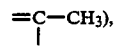

3.46(2H,s,C$_6$H$_5$C$\underline{H_2}$—), 3.61(3H,s,COOCH$_3$), 4.14(2H,t,J=6,—COOC$\underline{H_2}$CH$_2$—), 5.09(1H,s,C$_{(4)}$—H), 5.82(1H,s,NH).
Elemental analysis:
Calcd. for C$_{29}$H$_{34}$N$_4$O$_6$: C, 65.15; H, 6.41; N, 10.48.
Found: C, 64.93; H, 6.57; N, 10.48.

EXAMPLE 21

A mixture of m-nitrobenzaldehyde, 2-[4-(2-pyridyl)-1-piperazinyl]ethyl acetoacetate and methyl 3-aminocrotonate was worked up in isopropyl alcohol in the same manner as Example 1 to give methyl 2-[4-(2-pyridyl)-1-piperazinyl]ethyl 2,6-dimethyl-4-(3-nitrophenyl)-1,4-dihydropyridine-3,5-dicarboxylate as a light yellow powder, m.p. 53°-56° C. (sintering). Yield 54.5%. IR(Nujol)cm$^{-1}$: 3280. NMR(CDCl$_3$) δ: 2.35(3H,s,

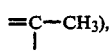

2.37(3H,s,

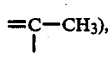

3.64(3H,s,COOCH$_3$), 4.21(2H,t,J=6,COOC$\underline{H_2}$CH$_2$—), 5.13(1H,s, C$_{(4)}$—H), 5.77(1H,s,NH).
Elemental analysis:
Calcd. for C$_{27}$H$_{31}$N$_5$O$_6$: C, 62.18; H, 5.99; N, 13.43.
Found: C, 62.20; H, 6.07; N, 13.03.

EXAMPLE 22

A mixture of m-chlorobenzaldehyde, 2-(4-benzhydryl-1-piperazinyl)ethyl acetoacetate and methyl 3-aminocrotonate was worked up in isopropyl alcohol in the same manner as Example 1 to give 2-(4-benzhydryl-1-piperazinyl)ethyl methyl 4-(3-chlorophenyl)-2,6-dimethyl-1,4-dihydropyridine-3,5-dicarboxylate as a light yellow powder, m.p. 74°-80° C. (sintering). Yield 28.3%. IR(Nujol)cm$^{-1}$: 3325, 1695, 1680. NMR(CDCl$_3$) δ: 2.32(6H,s,

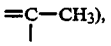

3.60(3H,s,COOCH$_3$), 4.96(1H,s,C$_{(4)}$—H), 5.64(1H,broad s, NH).
Elemental analysis:
Calcd. for C$_{35}$H$_{38}$ClN$_3$O$_4$: C, 70.04; H, 6.38; N, 7.00.
Found: C, 70.15; H, 6.29; N, 7.18.

EXAMPLE 23

A mixture of m-trifluoromethylbenzaldehyde, 2-(4-benzhydryl-1-piperazinyl)ethyl acetoacetate and methyl 3-aminocrotonate was worked up in isopropyl alcohol in the same manner as Example 1 to give 2-(4-benzhydryl-1-piperazinyl)ethyl methyl 2,6-dimethyl-4-(3-trifluoromethylphenyl)-1,4-dihydropyridine-3,5-dicarboxylate as a light yellow powder, m.p. 70°–72° C. Yield 52.5%. The product was further treated with methanolic hydrogen chloride and recrystallized from methanolethyl ether to give the dihydrochloride as colorless crystals, m.p. 168°–170° C.

Elemental analysis:
Calcd. for $C_{36}H_{38}F_3N_3O_4 \cdot 2HCl \cdot \frac{1}{2}H_2O$: C, 60.42; H, 5.77; N, 5.87.
Found: C, 60.52; H, 5.49; N, 5.66.

EXAMPLE 24

A mixture of 2,3-dichlorobenzaldehyde, 2-[4-(4,4'-dimethylbenzhydryl)-1-piperazinyl]ethyl acetoacetate and ethyl 3-aminocrotonate was worked up in isopropyl alcohol in the same manner as Example 1 to give 2-[4-(4,4'-dimethylbenzhydryl)-1-piperazinyl]ethyl ethyl 4-(2,3-dichlorophenyl)-2,6-dimethyl-1,4-dihydropyridine-3,5-dicarboxylate as a light yellow powder, m.p. 85°–88° C. (sintering). Yield 27.3%. IR(Nujol)cm$^{-1}$: 3330, 1690. NMR(CDCl$_3$) δ: 1.14(3H,t,J=7,—CH$_2$CH$_3$), 2.25(12H,s,

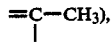

4.05(2H,q,J=7,—CH$_2$CH$_3$), 4.08(1H,s,>N—CH<), 4.08(2H,t, J=6,—COOCH$_2$CH$_2$—), 5.41(1H,s,C$_{(4)}$—H), 5.68(1H,broad s, NH).

Elemental analysis:
Calcd. for $C_{38}H_{43}Cl_2N_3O_4$: C, 67.45; H, 6.41; N, 6.21.
Found: C, 67.29; H, 6.27; N, 6.00.

EXAMPLE 25

A mixture of nicotinaldehyde, 2-(4-benzhydryl-1-piperazinyl)ethyl acetoacetate and methyl 3-aminocrotonate was worked up in isopropyl alcohol in the same manner as Example 1 to give 2-(4-benzhydryl-1-piperazinyl)ethyl methyl 2,6-dimethyl-4-(3-pyridyl)-1,4-dihydropyridine-3,5-dicarboxylate. Recrystallization from methanol gave colorless crystals, m.p. 227°–228° C. Yield 46.3%.

Elemental analysis:
Calcd. for $C_{34}H_{38}N_4O_4$: C, 72.06; H, 6.76; N, 9.89.
Found: C, 72.08; H, 6.73; N, 9.94.

EXAMPLE 26

(1) To a mixture of m-nitrobenzaldehyde (307 mg), 2-(4-benzhydryl-1-piperazinyl)ethyl acetoacetate (668 mg) and benzene (20 ml) was added piperidine (two drops), and the mixture was refluxed for 2 hours under removal of water using a Dean-Stark trap. After cooling, the reaction mixture was washed with water and dried over anhydrous sodium sulfate and the solvent was distilled off to give crude 2-(4-benzhydryl-1-piperazinyl)ethyl 2-(3-nitrobenzylidene)acetoacetate as an oil. NMR(CDCl$_3$) δ: 2.38(3H,s,COCH$_3$), 4.14–4.53(3H,m,—COOCH$_2$CH$_2$—,>N—CH<), 7.10–8.75(14H,m). This product was submitted to the next reaction step without further purification.

(2) The oil (whole amount) obtained in the above (1) and methyl 3-aminocrotonate (280 mg) were dissolved in isopropyl alcohol (10 ml) and the solution was refluxed for 2 hours. The solvent was distilled off and the residue was purified by silica gel chromatography to give 2-(4-benzhydryl-1-piperazinyl)ethyl methyl 2,6-dimethyl-4-(3-nitrophenyl)-1,4-dihydropyridine-3,5-dicarboxylate (725 mg, 67.6%). This product was further treated in the same manner as Example 1 to give the dihydrochloride. Recrystallization gave light yellow crystals, m.p. 166°–169° C. The IR and NMR spectra of this compound were identical with those of the dihydrochloride monohydrate obtained in Example 1.

EXAMPLE 27

(1) To a solution of 2-(4-benzhydryl-1-piperazinyl)ethyl acetoacetate (3.21 g) in ethanol (5 ml), 20% ethanolic ammonia (15 ml) was added, and the mixture was allowed to stand in a refrigerator overnight. The solvent and ammonia were distilled off to give crude 2-(4-benzhydryl-1-piperazinyl)ethyl 3-aminocrotonate as an oil.

(2) The oil obtained in the above (1), m-nitrobenzaldehyde (0.88 g) and methyl acetoacetate (1.15 g) were dissolved in isopropyl alcohol (15 ml), and the solution was refluxed with stirring for 6 hours. The solvent was distilled off and the residue was purified by silica gel chromatography. The product obtained was further treated in the same manner as Example 1 to give the dihydrochloride. By this procedure were obtained crystals of 2-(4-benzhydryl-1-piperazinyl)ethyl methyl 2,6-dimethyl-4-(3-nitrophenyl)-1,4-dihydropyridine-3,5-dicarboxylate dihydrochloride monohydrate (1.06 g, 17.8%), m.p. 166°–170° C. The IR and NMR spectra of this compound were identical with those of the compound obtained in Example 1.

EXAMPLE 28

A mixture of m-chlorobenzaldehyde, 2-(4-benzhydryl-1-piperazinyl)ethyl acetoacetate and ethyl 3-aminocrotonate was worked up in isopropyl alcohol in the same manner as Example 1 to give 2-(4-benzhydryl-1-piperazinyl)ethyl ethyl 4-(3-chlorophenyl)-2,6-dimethyl-1,4-dihydropyridine-3,5-dicarboxylate as a light yellow powder, m.p. 72°–75° C. (sintering). Yield 43.3%.

This product was dissolved in a small amount of ethanol, an excess amount of ethanolic hydrogen chloride was added thereto, and the mixture was allowed to stand. The resulting crystalline precipitate was dissolved in chloroform-methanol (3:1, v/v) and the solution was concentrated. Addition of ethyl acetate gave crystals of 2-(4-benzhydryl-1-piperazinyl)ethyl ethyl 4-(3-chlorophenyl)-2,6-dimethyl-1,4-dihydropyridine-3,5-dicarboxylate dihydrochloride, m.p. 179°–182° C.

Elemental analysis:
Calcd. for $C_{36}H_{40}ClN_3O_4 \cdot 2HCl$: C, 62.93; H, 6.16; N, 6.12.
Found: C, 62.67; H, 6.44; N, 6.00.

EXAMPLE 29

A mixture of p-chlorobenzaldehyde, 2-(4-benzhydryl-1-piperazinyl)ethyl acetoacetate and ethyl 3-aminocrotonate was worked up in isopropyl alcohol in the same manner as Example 1 to give 2-(4-benzhydryl-1-piperazinyl)ethyl ethyl 4-(4-chlorophenyl)-2,6-dimethyl-1,4-dihydropyridine-3,5-dicarboxylate as a yellow powder, m.p. 75°–79° C. (sintering). Yield 32.8%. IR(Nujol)cm$^{-1}$: 3300, 1695, 1670. NMR(CDCl$_3$) δ: 1.17(3H,t,J=7.5,—CH$_2$CH$_3$), 2.28(6H,s,

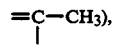

4.95(1H,s,C$_{(4)}$—H), 5.77(1H,broad s, NH).
Elemental analysis:
Calcd. for C$_{36}$H$_{40}$ClN$_3$O$_4$: C, 70.40; H, 6.56; N, 6.84.
Found: C, 70.04; H, 6.51; N, 6.82.

EXAMPLE 30

A mixture of m-nitrobenzaldehyde, 2-(4-benzhydryl-1-piperazinyl)ethyl acetoacetate and 2-methoxyethyl 3-aminocrotonate was worked up in isopropyl alcohol in the same manner as Example 1 to give 2-(4-benzhydryl-1-piperazinyl)ethyl 2-methoxyethyl 2,6-dimethyl-4-(3-nitrophenyl)-1,4-dihydropyridine-3,5-dicarboxylate as a light yellow powder, m.p. 62°–66° C. (sintering). Yield 19.5%. IR(Nujol)cm$^{-1}$: 3300, 1685, 1675. NMR(CDCl$_3$) δ: 2.33(6H,s,

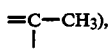

2.5(2H,t,J=6,—CH$_2$CH$_2$N>), 3.29(3H, s,OCH$_3$), 3.49(2H,t,J=4.5,—CH$_2$CH$_2$O—), 5.08(1H,s,C$_{(4)}$—H), 5.77(1H,broad s, NH).
Elemental analysis:
Calcd. for C$_{37}$H$_{42}$N$_4$O$_7$: C, 67.87; H, 6.47; N, 8.56.
Found: C, 67.69; H, 6.49; N, 8.30.

EXAMPLE 31

A mixture of m-nitrobenzaldehyde, 2-[4-(4,4'-dimethylbenzhydryl)-1-piperazinyl]ethyl acetoacetate and ethyl 3-aminocrotonate was worked up in isopropyl alcohol in the same manner as Example 1 to give 2-[4-(4,4'-dimethylbenzhydryl)-1-piperazinyl]ethyl ethyl 2,6-dimethyl-4-(3-nitrophenyl)-1,4-dihydropyridine-3,5-dicarboxylate as a light yellow powder, m.p. 82°–85° C. (sintering). Yield 50.8%. IR(Nujol)cm$^{-1}$: 3330, 1685. NMR(CDCl$_3$) δ: 1.19(3H,t,J=7,—CH$_2$CH$_3$), 2.26(6H,s,

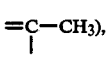

2.33(6H,s,

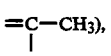

4.05(2H,q,J=7,—CH$_2$CH$_3$), 4.10(1H,s,>N—CH<), 4.12(2H,t,J=6,—COOCH$_2$CH$_2$—), 5.07(1H,s,C$_{(4)}$—H), 5.75(1H, broad s, NH).
Elemental analysis:
Calcd. for C$_{38}$H$_{44}$N$_4$O$_6$: C, 69.92; H, 6.79; N, 8.58.
Found: C, 69.94; H, 6.75; N, 8.25.

EXAMPLE 32

A mixture of m-trifluoromethylbenzaldehyde, 2-[4-(4,4'-dimethylbenzhydryl)-1-piperazinyl]ethyl acetoacetate and ethyl 3-aminocrotonate was worked up in isopropyl alcohol in the same manner as Example 1 to give 2-[4-(4,4'-dimethylbenzhydryl)-1-piperazinyl]ethyl ethyl 2,6-dimethyl-4-(3-trifluoromethylphenyl)-1,4-dihydropyridine-3,5-dicarboxylate as a colorless powder, m.p. 74°–77° C. (sintering). Yield 44.1%. IR(Nujol)cm$^{-1}$: 3320, 1680. NMR(CDCl$_3$) δ: 1.17(3H,t,J=7,—CH$_2$CH$_3$), 2.26(6H,s,

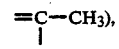

2.32(6H,s,

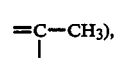

4.05(2H,q,J=7,—CH$_2$CH$_3$), 4.10(1H,s,>N—CH<), 4.12(2H,t,J=6,—COOCH$_2$CH$_2$—), 5.02(1H,s,C$_{(4)}$—H), 5.65(1H, broad s, NH).
Elemental analysis:
Calcd. for C$_{39}$H$_{44}$F$_3$N$_3$O$_4$: C, 69.32; H, 6.56; N, 6.22.
Found: C, 69.23; H, 6.55; N, 6.07.

EXAMPLE 33

A mixture of m-chlorobenzaldehyde, 2-[4-(4,4'-dimethylbenzhydryl)-1-piperazinyl]ethyl acetoacetate and ethyl 3-aminocrotonate was worked up in isopropyl alcohol in the same manner as Example 1 to give 2-[4-(4,4'-dimethylbenzhydryl)-1-piperazinyl]ethyl ethyl 4-(3-chlorophenyl)-2,6-dimethyl-1,4-dihydropyridine-3,5-dicarboxylate as a colorless powder, m.p. 79°–81° C. (sintering). Yield 48.4%. IR(Nujol)cm$^{-1}$: 3330, 1680. NMR(CDCl$_3$) δ: 1.16(3H,t,J=7,—CH$_2$CH$_3$), 2.22(6H,s,

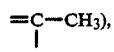

2.28(6H,s,

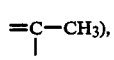

4.05(2H,q,J=7,—CH$_2$CH$_3$), 4.08(1H,s,>N—CH<), 4.11(2H,t,J=6,—COOCH$_2$CH$_2$—), 4.93(1H,s,C$_{(4)}$—H), 5.64(1H, broad s, NH).
Elemental analysis:
Calcd. for C$_{38}$H$_{44}$ClN$_3$O$_4$: C, 71.07; H, 6.91; N, 6.54.
Found: C, 71.19; H, 6.87; N, 6.38.

EXAMPLE 34

A mixture of m-anisaldehyde, 2-[4-(4,4'-dimethylbenzhydryl)-1-piperazinyl]ethyl acetoacetate and ethyl 3-aminocrotonate was worked up in isopropyl alcohol in the same manner as Example 1 to give 2-[4-(4,4'-dimethylbenzhydryl)-1-piperazinyl]ethyl ethyl 4-(3-methoxyphenyl)-2,6-dimethyl-1,4-dihydropyridine-3,5-dicarboxylate as a colorless powder, m.p. 75°–78° C. (sintering). Yield 42.2%. IR(Nujol)cm$^{-1}$: 3330, 1690. NMR(CDCl$_3$) δ: 1.18(3H,t, J=7,—CH$_2$CH$_3$), 2.25(6H,s,

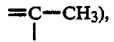

2.27(3H,s, 2.29(3H,s, 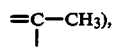

3.68(3H,s,—OCH₃), 4.05(2H,q,—CH₂CH₃), 4.09(1H,s,>N—CH<), 4.14(2H,t,J=6,—COOCH₂CH₂—), 4.96(1H, s,C₍₄₎—H), 5.62(1H,broad s, NH).
Elemental analysis:
Calcd. for $C_{39}H_{47}N_3O_5$: C, 73.44; H, 7.43; N, 6.59.
Found: C, 73.09; H, 7.64; N, 6.41.

EXAMPLE 35

A mixture of m-methoxycarbonylbenzaldehyde, 2-[4-(4,4'-dimethylbenzhydryl)-1-piperazinyl]ethyl acetoacetate and ethyl 3-aminocrotonate was worked up in isopropyl alcohol in the same manner as Example 1 to give 2-[4-(4,4'-dimethylbenzhydryl)-1-piperazinyl]ethyl ethy 4-(3-methoxycarbonylphenyl)-2,6-dimethyl-1,4-dihydropyridine-3,5-dicarboxylate as a light yellow powder, m.p. 80°–83° C. (sintering). Yield 47.5%. IR(Nujol)cm⁻¹: 3330, 1720, 1690. NMR(CDCl₃) δ: 1.17(3H,t,J=7,—CH₂CH₃), 2.25(6H,s,

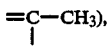

2.31(6H,s,

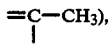

3.83(3H,s,—COOCH₃), 4.03(2H, q,J=7,—CH₂CH₃), 4.10(1H,s,>N—CH<), 4.10(2H,t,J=6, —COOCH₂CH₂—), 5.00(1H,s,C₍₄₎—H), 5.78(1H,broad s, NH).
Elemental analysis:
Calcd. for $C_{40}H_{47}N_3O_6$: C, 72.12; H, 7.12; N, 6.31.
Found: C, 71.74; H, 7.24; N, 6.12.

EXAMPLE 36

A mixture of p-cyanobenzaldehyde, 2-[4-(4,4'-dimethylbenzhydryl)-1-piperazinyl]ethyl acetoacetate and ethyl 3-aminocrotonate was worked up in isopropyl alcohol in the same manner as Example 1 to give 2-[4-(4,4'-dimethylbenzhydryl)-1-piperazinyl]ethyl ethyl 4-(4-cyanophenyl)-2,6-dimethyl-1,4-dihydropyridine-3,5-dicarboxylate as a light yellow powder, m.p. 93°–96° C. (sintering). Yield 61.9. IR(Nujol)cm⁻¹: 3330, 2220, 1685. NMR(CDCl₃) δ: 1.15(3H,t,J=7,—CH₂CH₃), 2.24(6H,s,

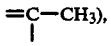

2.29(6H,s, 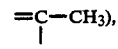

4.03(2H,q,J=7,—CH₂CH₃), 4.11(1H,s,>N—CH<), 4.13(2H,t,J=7,—COOCH₂—), 5.01(1H, s,C₍₄₎—H), 5.77(1H,broad s, NH).
Elemental analysis:
Calcd. for $C_{39}H_{44}N_4O_4$: C, 74.02; H, 7.01; N, 8.86.
Found: C, 74.07; H, 7.22; N, 9.06.

EXAMPLE 37

A mixture of m-nitrobenzaldehyde, 3-(4-benzhydryl-1-piperazinyl)propyl acetoacetate and methyl 3-aminocrotonate was worked up in isopropyl alcohol in the same manner as Example 1 to give 3-(4-benzhydryl-1-piperazinyl)propyl methyl 2,6-dimethyl-4-(3-nitrophenyl)-1,4-dihydropyridine-3,5-dicarboxylate as an oil. This product was further treated with methanolic hydrogen chloride. Recrystallization from methanol gave the dihydrochloride as light yellow crystals, m.p. 168°–173° C. Yield 34.3%.
Elemental analysis:
Calcd. for $C_{36}H_{40}N_4O_6 \cdot 2HCl \cdot \frac{1}{2}H_2O$: C, 61.19; H, 6.13; N, 7.93.
Found: C, 61.09; H, 6.07; N, 7.93.

EXAMPLE 38

A mixture of m-chlorobenzaldehyde, 3-(4-benzhydryl-1-piperazinyl)propyl acetoacetate and methyl 3-aminocrotonate was worked up in isopropyl alcohol in the same manner as Example 1 to give 3-(4-benzhydryl-1-piperazinyl)propyl methyl 4-(3-chlorophenyl)-2,6-dimethyl-1,4-dihydropyridine-3,5-dicarboxylate as an oil. This product was further treated with methanolic hydrogen chloride. Recrystallization from methanol gave the dihydrochloride as colorless crystals, m.p. 169°–172° C. Yield 45.6%.
Elemental analysis:
Calcd. for $C_{36}H_{40}ClN_3O_4 \cdot 2HCl$: C, 62.93; H, 6.16; N, 6.12.
Found: C, 62.89; H, 6.36; N, 6.07.

EXAMPLE 39

A mixture of furfural, 3-(4-benzhydryl-1-piperazinyl)ethyl acetoacetate and methyl 3-aminocrotonate was worked up in isopropyl alcohol in the same manner as Example 1 to give 3-(4-benzhydryl-1-piperazinyl)ethyl methyl 4-(2-furyl)-2,6-dimethyl-1,4-dihydropyridine-3,5-dicarboxylate as a light yellow powder, m.p. 71°–77° C. (sintering). Yield 33.4%. IR(Nujol)cm⁻¹: 3310, 1700, 1685. NMR(CDCl₃) δ: 2.30(6H,s,

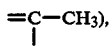

2.64(2H,t,J=6,

3.62(3H,s,OCH₃), 5.16(1H,s,C₍₄₎—H), 5.77(broad s, NH).
Elemental analysis:
Calcd. for $C_{33}H_{37}N_3O_5$: C, 71.33; H, 6.71; N, 7.56.

Found: C, 71.02; H, 6.69; N, 7.64.

EXAMPLE 40

A mixture of 5-methyl-2-thiophenecarbaldehyde, 2-[4-(4,4'-dimethylbenzhydryl)-1-piperazinyl]ethyl acetoacetate and ethyl 3-aminocrotonate was worked up in isopropyl alcohol in the same manner as Example 1 to give 2-[4-(4,4'-dimethylbenzhdryl)-1-piperazinyl]ethyl ethyl 2,6-dimethyl-4-(5-methyl-2-thienyl)-1,4-dihydropyridine-3,5-dicarboxylate as a light yellow powder, m.p. 82°–85° C. (sintering). Yield 25.8%. IR(Nujol)cm$^{-1}$: 3330, 1690. NMR(CDCl$_3$) δ: 1.22(3H,t,J=7,—CH$_2$CH$_3$), 2.24(6H,s,

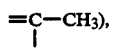

2.28(6H,s,

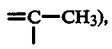

2.30(3H,s,

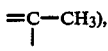

4.10(1H,s,>N—CH<), 4.13(2H,q,J=7,—CH$_2$CH$_3$). 4.20(2H,t,J=6,—COOCH$_2$CH$_2$—), 5.20(1H,s,C$_{(4)}$—H), 5.75(1H,broad s, NH).

Elemental analysis:
Calcd. for C$_{37}$H$_{45}$N$_3$O$_4$S: C, 70.79; H, 7.23; N, 6.69.
Found: C, 70.76; H, 7.30; N, 6.51.

EXAMPLE 41

A mixture of m-nitrobenzaldehyde, 2-[4-(4-fluorophenyl)-1-piperazinyl]ethyl acetoacetate and ethyl 3-aminocrotonate was worked up in isopropyl alcohol in the same manner as Example 1 to give ethyl 2-[4-(4-fluorophenyl)-1-piperazinyl]ethyl 2,6-dimethyl-4-(3-nitrophenyl)-1,4-dihydropyridine-3,5-dicarboxylate as yellow crystals, m.p. 129°–131.5° C. (recrystallized from ethyl acetate-hexane). Yield 45.3%.

Elemental analysis:
Calcd. for C$_{29}$H$_{33}$FN$_4$O$_6$: C, 63.03; H, 6.02; N, 10.14.
Found: C, 62.95; H, 6.10; N, 10.10.

EXAMPLE 42

A mixture of m-chlorobenzaldehyde, 2-[4-(4-fluorophenyl)-1-piperazinyl]ethyl acetoacetate and methyl 3-aminocrotonate was worked up in isopropyl alcohol in the same manner as Example 1 to give 2-[4-(4-fluorophenyl)-1-piperazinyl]ethyl methyl 4-(3-chlorophenyl)-2,6-dimethyl-1,4-dihydropyridine-3,5-dicarboxylate as a light yellow powder, m.p. 44°–49° C. (sintering). Yield 34.1%. IR(Nujol)cm$^{-1}$: 3430, 1700, 1685. NMR(CDCl$_3$) δ: 2.30(3H,s,

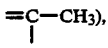

2.34(3H,s,

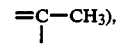

3.63(3H,s,—COOCH$_3$), 4.18(2H,t,J=6,—COOCH$_2$CH$_2$—), 4.99(1H,s,C$_{(4)}$—H), 5.69(1H,s,NH).

Elemental analysis:
Calcd. for C$_{29}$H$_{33}$ClFN$_3$O$_4$: C, 64.26; H, 6.14; N, 7.75.
Found: C, 63.96; H, 5.94; N, 7.48.

EXAMPLE 43

A mixture of 2,3-dichlorobenzaldehyde, 2-[4-(4-fluorophenyl)-1-piperazinyl]ethyl acetoacetate and methyl 3-aminocrotonate was worked up in isopropyl alcohol in the same manner as Example 1 to give 2-[4-(4-fluorophenyl)-1-piperazinyl]ethyl methyl 4-(2,3-dichlorophenyl)-2,6-dimethyl-1,4-dihydropyridine-3,5-dicarboxylate as colorless prisms, m.p. 146°–148° C. (recrystallized from ethyl acetate-ethyl ether). Yield 34.9%.

Elemental analysis:
Calcd. for C$_{28}$H$_{30}$FCl$_2$N$_3$O$_4$: C, 59.79; H, 5.38; N, 7.47.
Found: C, 59.84; H, 5.40; N, 7.16.

EXAMPLE 44

A mixture of m-nitrobenzaldehyde, 2-[4-(2-chlorophenyl)-1-piperazinyl]ethyl acetoacetate and methyl 3-aminocrotonate was worked up in isopropyl alcohol in the same manner as Example 1 to give 2-[4-(2-chlorophenyl)-1-piperazinyl]ethyl methyl 2,6-dimethyl-4-(3-nitrophenyl)-1,4-dihydropyridine-3,5-dicarboxylate as yellow crystals, m.p. 153°–154° C. (recrystallized from ethyl ether-hexane). Yield 46.5%.

Elemental analysis:
Calcd. for C$_{28}$H$_{31}$ClN$_4$O$_6$: C, 60.59; H, 5.63; N, 10.09.
Found: C, 60.47; H, 5.84; N, 9.91.

EXAMPLE 45

A mixture of m-nitrobenzaldehyde, 2-[4-(4-chlorophenyl)-1-piperazinyl]ethyl acetoacetate and methyl 3-aminocrotonate was worked up in isopropyl alcohol in the same manner as Example 1 to give 2-[4-(4-chlorophenyl)-1-piperazinyl]ethyl methyl 2,6-dimethyl-4-(3-nitrophenyl)-1,4-dihydropyridine-3,5-dicarboxylate as light yellow crystals, m.p. 141.5°–143° C. (recrystallized from ethyl ether-hexane). Yield 55.7%.

Elemental analysis:
Calcd. for C$_{28}$H$_{31}$ClN$_4$O$_6$: C, 60.59; H, 5.63; N, 10.09.
Found: C, 60.52; H, 5.74; N, 9.83.

EXAMPLE 46

A mixture of 2,3-dichlorobenzaldehyde, 2-[4-(3-chlorophenyl)-1-phiperazinyl]ethyl acetoacetate and methyl 3-aminocrotonate was worked up in isopropyl alcohol in the same manner as Example 1 to give 2-[4-(3-chlorophenyl)-1-piperazinyl]ethyl methyl 2,6-dimethyl-4-(3-nitrophenyl)-1,4-dihydropyridine-3,5-dicarboxylate as colorless prisms, m.p. 140°–143° C. (recrystallized from ethyl ether-hexane). Yield 29.2%.

Elemental analysis:
Calcd. for C$_{28}$H$_{30}$Cl$_3$N$_3$O$_4$: C, 58.09; H, 5.22; N, 7.26.
Found: C, 58.23; H, 5.25; N, 6.87.

EXAMPLE 47

A mixture of m-trifluoromethylbenzaldehyde, 2-[4-(3-chlorophenyl)-1-piperazinyl]ethyl acetoacetate and methyl 3-aminocrotonate was worked up in isopropyl alcohol in the same manner as Example 1 to give 2-[4-(3-chlorophenyl)-1-piperazinyl]ethyl methyl 2,6-dimethyl-4-(3-trifluoromethylphenyl)-1,4-dihydropyridine-3,5-dicarboxylate as colorless prisms, m.p. 141°-143° C. (recrystallized from ethyl ether-hexane). Yield 44.6%.
Elemental analysis:
Calcd. for $C_{29}H_{31}ClF_3N_3O_4$: C, 60.26; H, 5.41; N, 7.27.
Found: C, 60.13; H, 5.51; N, 6.95.

EXAMPLE 48

A mixture of o-chlorobenzaldehyde, 2-[4-(3-chlorophenyl)-1-piperazinyl]ethyl acetoacetate and methyl 3-aminocrotonate was worked up in isopropyl alcohol in the same manner as Example 1 to give 2-[4-(3-chlorophenyl)-1-piperazinyl]ethyl methyl 4-(2-chlorophenyl)-2,6-dimethyl-1,4-dihydropyridine-3,5-dicarboxylate as colorless prisms, m.p. 130°-132° C. (recrystallized from isopropyl ether-hexane). Yield 24.1%.
Elemental analysis:
Calcd. for $C_{28}H_{31}Cl_2N_3O_4$:
C, 61.77; H, 5.74; N, 7.72.
Found: C, 62.06; H, 5.74; N, 7.69.

EXAMPLE 49

A mixture of m-chlorobenzaldehyde, 2-[4-(2-chlorophenyl)-1-piperazinyl]ethyl acetoacetate and methyl 3-aminocrotonate was worked up in isopropyl alcohol in the same manner as Example 1 to give 2-[4-(2-chlorophenyl)-1-piperazinyl]ethyl methyl 4-(3-chlorophenyl)-2,6-dimethyl-1,4-dihydropyridine-3,5-dicarboxylate as colorless prisms, m.p. 161.5°-163° C. (recrystallized from isopropyl ether-hexane). Yield 52.6%.
Elemental analysis:
Calcd. for $C_{28}H_{31}Cl_2N_3O_4$:
C, 61.77; H, 5.74; N, 7.72.
Found: C, 61.86; H, 5.73; N, 7.58.

EXAMPLE 50

A mixture of m-chlorobenzaldehyde, 2-[4-(4-chlorophenyl)-1-piperazinyl]ethyl acetoacetate and methyl 3-aminocrotonate was worked up in isopropyl alcohol in the same manner as Example 1 to give 2-[4-(4-chlorophenyl)-1-piperazinyl]ethyl methyl 4-(3-chlorophenyl)-2,6-dimethyl-1,4-dihydropyridine-3,5-dicarboxylate as colorless crystals, m.p. 127°-131° C. (recrystallized from isopropyl ether-hexane). Yield 47.5%.
Elemental analysis:
Calcd. for $C_{28}H_{31}Cl_2N_3O_4$:
C, 61.77; H, 5.74; N, 7.72.
Found: C, 61.81; H, 5.93; N, 7.73.

EXAMPLE 51

A mixture of m-nitrobenzaldehyde, 2-[4-(2-methylphenyl)-1-piperazinyl]ethyl acetoacetate and methyl 3-aminocrotonate was worked up in isopropyl alcohol in the same manner as Example 1 to give methyl 2-[4-(2-methylphenyl)-1-piperazinyl]ethyl 2,6-dimethyl-4-(3-nitrophenyl)-1,4-dihydropyridine-3,5-dicarboxylate as colorless crystals, m.p. 156°-157° C. (recrystallized from isopropyl ether-hexane). Yield 72.1%.
Elemental analysis:
Calcd. for $C_{29}H_{34}N_4O_6$:
C, 65.15; H, 6.41; N, 10.48.
Found: C, 64.98; H, 6.40; N, 10.27.

EXAMPLE 52

A mixture of m-chlorobenzaldehyde, 2-[4-(2-methylphenyl)-1-piperazinyl]ethyl acetoacetate and methyl 3-aminocrotonate was worked up in isopropyl alcohol in the same manner as Example 1 to give methyl 2-[4-(2-methylphenyl)-1-piperazinyl]ethyl 4-(3-chlorophenyl)-2,6-dimethyl-1,4-dihydropyridine-3,5-dicarboxylate as colorless crystals, m.p. 151°-153° C. (recrystallized from isopropyl ether-hexane). Yield 48.6%.
Elemental analysis:
Calcd. for $C_{29}H_{34}ClN_3O_4$:
C, 66.47; H, 6.54; N, 8.02.
Found: C, 66.47; H, 6.55; N, 7.79.

EXAMPLE 53

A mixture of m-nitrobenzaldehyde, 2-(4-phenyl-1-piperazinyl)ethyl acetoacetate and methyl 3-aminocrotonate was worked up in isopropyl alcohol in the same manner as Example 1 to give methyl 2-(4-phenyl-1-piperazinyl)ethyl 2,6-dimethyl-4-(3-nitrophenyl)-1,4-dihydropyridine-3,5-dicarboxylate as yellow crystals, m.p. 113°-118° C. (recrystallized from isopropyl ether-hexane). Yield 51.2%.
Elemental analysis:
Calcd. for $C_{28}H_{32}N_4O_6$:
C, 64.60; H, 6.20; N, 10.76.
Found: C, 64.41; H, 6.16; N, 10.58.

EXAMPLE 54

A mixture of m-chlorobenzaldehyde, 2-(4-phenyl-1-piperazinyl)ethyl acetoacetate and methyl 3-aminocrotonate was worked up in isopropyl alcohol in the same manner as Example 1 to give methyl 2-(4-phenyl-1-piperazinyl)ethyl 4-(3-chlorophenyl)-2,6-dimethyl-1,4-dihydropyridine-3,5-dicarboxylate as colorless crystals, m.p. 147°-148.5° C. (recrystallized from isopropyl ether-hexane). Yield 44.2%.
Elemental analysis:
Calcd. for $C_{28}H_{32}ClN_3O_4$:
C, 65.94; H, 6.32; N, 8.24.
Found: C, 65.86; H, 6.25; N, 8.17.

EXAMPLE 55

A mixture of m-nitrobenzaldehyde, 2-[4-(4-methoxyphenyl)-1-piperazinyl]ethyl acetoacetate and methyl 3-aminocrotonate was worked up in isopropyl alcohol in the same manner as Example 1 to give 2-[4-(4-methoxyphenyl)-1-piperazinyl]ethyl methyl 2,6-dimethyl-4-(3-nitrophenyl)-1,4-dihydropyridine-3,5-dicarboxylate as yellow prisms, m.p. 169°-171° C. (recrystallized from isopropyl ether). Yield 62.1%.
Elemental analysis:
Calcd. for $C_{29}H_{34}N_4O_7$:
C, 63.26; H, 6.22; N, 10.18.
Found: C, 63.10; H, 6.28; N, 10.16.

EXAMPLE 56

A mixture of m-chlorobenzaldehyde, 2-[4-(4-methoxyphenyl)-1-piperazinyl]ethyl acetoacetate and methyl 3-aminocrotonate was worked up in the same manner as Example 1 to give 2-[4-(4-methoxyphenyl)-1-piperazinyl]ethyl methyl 4-(3-chlorophenyl)-2,6-dimethyl-1,4-dihydropyridine-3,5-dicarboxylate as colorless prisms, m.p. 163.5°-164.5° C. (recrystallized from isopropyl ether). Yield 50.9%.

Elemental analysis:
Calcd. for $C_{29}H_{34}ClN_3O_5$:
C, 64.50; H, 6.35; N, 7.78.
Found: C, 64.31; H, 6.28; N, 7.78.

EXAMPLE 57

A mixture of m-nitrobenzaldehyde, 2-[4-(3-chloro-4-methylphenyl)-1-piperazinyl]ethyl acetoacetate and methyl 3-aminocrotonate was worked up in isopropyl alcohol in the same manner as Example 1 to give 2-[4-(3-chloro-4-methylphenyl)-1-piperazinyl]ethyl methyl 2,6-dimethyl-4-(3-nitrophenyl)-1,4-dihydropyridine-3,5-dicarboxylate as yellow crystals, m.p. 155°–157° C. (recrystallized from ethyl ether-hexane). Yield 54.8%.
Elemental analysis:
Calcd. for $C_{29}H_{33}ClN_4O_6$:
C, 61.21; H, 5.85; N, 9.85.
Found: C, 61.35; H, 5.87; N, 9.78.

EXAMPLE 58

A mixture of m-nitrobenzaldehyde, 2-[4-(2,3-dichlorophenyl)-1-piperazinyl]ethyl acetoacetate and methyl 3-aminocrotonate was worked up in isopropyl alcohol in the same manner as Example 1 to give 2-[4-(2,3-dichlorophenyl)-1-piperazinyl]ethyl methyl 2,6-dimethyl-4-(3-nitrophenyl)-1,4-dihydropyridine-3,5-dicarboxylate as yellow crystals, m.p. 189°–190° C. Yield 75.7%.
Elemental analysis:
Calcd. for $C_{28}H_{30}Cl_2N_4O_6$:
C, 57.05; H, 5.13; N, 9.50.
Found: C, 56.99; H, 5.12; N, 9.47.

EXAMPLE 59

A mixture of m-nitrobenzaldehyde, 2-[4-(2,5-dichlorophenyl)-1-piperazinyl]ethyl acetoacetate and methyl 3-aminocrotonate was worked up in isopropyl alcohol in the same manner as Example 1 to give 2-[4-(2,5-dichlorophenyl)-1-piperazinyl]ethyl methyl 2,6-dimethyl-4-(3-nitrophenyl)-1,4-dihydropyridine-3,5-dicarboxylate as yellow crystals, m.p. 170°–172° C. (recrystallized from isopropyl ether-hexane). Yield 54.9%.
Elemental analysis:
Calcd. for $C_{28}H_{30}Cl_2N_4O_6$:
C, 57.05; H, 5.13; N, 9.50.
Found: C, 56.88; H, 5.14; N, 9.17.

EXAMPLE 60

A mixture of 2,1,3-benzoxadiazole-4-carbaldehyde, 2-(4-benzhydryl-1-piperazinyl)ethyl acetoacetate and methyl 3-aminocrotonate was worked up in isopropyl alcohol in the same manner as Example 1 and the product obtained was further treated with methanolic hydrogen chloride solution to give 2-(4-benzhydryl-1-piperazinyl)ethyl methyl 4-(2,1,3-benzoxadiazol-4-yl)-2,6-dimethyl-1,4-dihydropyridine-3,5-dicarboxylate dihydrochloride as light yellow crystals, m.p. 192°–198° C. Yield 45.0%.
Elemental analysis:
Calcd. for $C_{35}H_{37}N_5O_5\cdot 2HCl\cdot \frac{1}{2}H_2O$:
C, 60.96; H, 5.85; N, 10.16.
Found: C, 60.89; H, 5.55; N, 10.09.

EXAMPLE 61

The monohydrate obtained in Example 1 was dissolved in methanol and the solution was concentrated. Recrystallization from ethyl acetate gave anhydrous 2-(4-benzhydryl-1-piperazinyl)ethyl methyl 2,6-dimethyl-4-(3-nitrophenyl)-1,4-dihydropyridine-3,5-dicarboxylate dihydrochloride. M.p. 174°–180° C. [204°–206.5° C. (decompn.) when measured in a capillary tube].
Elemental analysis:
Calcd. for $C_{35}H_{38}N_4O_6\cdot 2HCl$:
C, 61.49; H, 5.90; N, 8.20.
Found: C, 61.50; H, 5.81; N, 8.32.

EXAMPLE 62

The free base obtained in Example 9 was dissolved in a small amount of methanol, an excess of hydrogen chloride in methanol was added thereto, and the mixture was concentrated. The residue was recrystallized from ethanolethyl ether to give 2-[4-(4,4'-dimethylbenzhydryl)-1-piperazinyl]ethyl methyl 2,6-dimethyl-4-(3-nitrophenyl)-1,4-dihydropyridine-3,5-dicarboxylate dihydrochloride as light yellow crystals, m.p. 182°–183° C.
Elemental analysis:
Calcd. for $C_{37}H_{42}N_4O_6\cdot 2HCl$:
C, 62.44; H, 6.23; N, 7.87.
Found: C, 62.31; H, 6.19; N, 7.90.

EXAMPLE 63

The free base obtained in Example 17 was added in a small amount of methanol, an excess of methanolic hydrogen chloride was added thereto, and the mixture was concentrated. The resulting crystalline precipitate was collected by filtration and recrystallized from methanol to give 2-[4-(3-chlorophenyl)-1-piperazinyl]ethyl methyl 2,6-dimethyl-4-(3-nitrophenyl)-1,4-dihydropyridine-3,5-dicarboxylate hydrochloride as yellow crystals, m.p. 192°–196° C.
Elemental analysis:
Calcd. for $C_{28}H_{31}ClN_4O_6\cdot HCl$:
C, 56.86; H, 5.45; N, 9.47; Cl, 11.99.
Found: C, 56.79; H, 5.48; N, 9.67; Cl, 11.85.

EXAMPLE 64

(1) To a solution of 2-(4-benzhydryl-1-piperazinyl)ethyl acetoacetate (3.0 g) in ethanol (15 ml) was added a 15% ethanolic ammonia solution (15 ml). The mixture was allowed to stand in a refrigerator for 2 days. The solvent and ammonia was distilled off to give crude 2-(4-benzhydryl-1-piperazinyl)ethyl 3-aminocrotonate as an oil. (2) The oil obtained in the above (1) and methyl 2-(3-nitrobenzylidene)acetoacetate (1.97 g) were dissolved in isopropyl alcohol (30 ml), and the solution was refluxed for 10 hours. The solvent was distilled off and the residue was purified by chromatography (silica gel). This product was converted to the dihydrochloride in the same manner as Example 1 to give 2-(4-benzhydryl-1-piperazinyl)ethyl methyl 2,6-dimethyl-4-(3-nitrophenyl)-1,4-dihydropyridine-3,5-dicarboxylate dihydrochloride monohydrate (0.83 g, 15%), m.p. 164°–169° C.

The IR and NMR spectra of this compound were identical with those of the dihydrochloride monohydrate obtained in Example 1.

FORMULATION EXAMPLE

For use as an antihypertensive drug, the compound (I) of this invention can be used in the following exemplary formulations.

A. Tablet

| | | |
|---|---|---|
| (1) | 2-(4-Benzhydryl-1-piperazinyl)ethyl methyl 2,6-dimethyl-4-(3-nitrophenyl)-1,4-dihydropyridine-3,5-dicarboxylate dihydrochloride monohydrate | 5 g |
| (2) | Lactose | 95 g |
| (3) | Corn starch | 29 g |
| (4) | Magnesium stearate | 1 g |
| | | 130 g for 1000 tablets |

The whole amounts of (1) and (2) are mixed with 17 g of corn starch (3) and the mixture is granulated with a paste prepared from 7 g of corn starch (3). Then 5 g of corn starch (3) and the whole amount of (4) are added and the whole mixture is compression molded on a compression tableting machine to give 1000 tablets 7 mm in diameter and each containing 5 mg of (1).

B. Capsule

| | | |
|---|---|---|
| (1) | 2-[4-(4,4'-Difluorobenzhydryl)-1-piperazinyl]ethyl methyl 2,6-dimethyl-4-(3-nitrophenyl)-1,4-dihydropyridine-3,5-dicarboxylate dihydrochloride | 5 g |
| (2) | Lactose | 140 g |
| (3) | Microcrystalline cellulose | 70 g |
| (4) | Magnesium stearate | 5 g |
| | | 220 g for 1000 capsules |

The whole amounts of the above components are mixed and filled into 1000 gelatin capsules No. 3 (Japanese Pharmacopeia IX) to give capsules each containing 5 mg of (1).

REFERENCE EXAMPLE 1

(1) To a mixture of 1-piperazineethanol (11.4 g), potassium carbonate powder (24.3 g) and N,N-dimethylformamide (100 ml) was added dropwise benzhydryl bromide (21.7 g) under stirring. The mixture was stirred at room temperature for 2 hours, diluted with water and extracted with ethyl ether. The ethyl ether layer was washed with saturated aqueous sodium chloride and dried over anhydrous sodium sulfate. The solvent was then distilled off and the residue was purified by silica gel chromatography [eluent: hexane-ethyl acetate (2:1)] to give 21.9 g (84.2%) of 4-benzhydryl-1-piperazineethanol as an oil. IR(Neat): 3380 cm$^{-1}$. NMR(CDCl$_3$)δ: 2.46(10H, broad s), 3.57(2H, t, J=6.5), 4.20(1H, s), 7.03–7.45(12H, m).

In the same manner as above, there were obtained the following compounds:

4-(4,4'-Difluorobenzhydryl)-1-piperazineethanol: Oil, IR(Neat): 3380 cm$^{-1}$. NMR(CDCl$_3$)δ: 2.2–2.7(10H, m), 3.54(2H, t, J=6), 4.18(1H, s), 6.8–7.4(8H, m).

4-(4,4'-Dichlorobenzhydryl)-1-piperazineethanol: Oil, IR(Neat): 3400 cm$^{-1}$. NMR(CDCl$_3$)δ: 2.2–2.6(10H, m), 2.82(1H, s, OH), 3.53(2H, t, J=6), 4.14(1H, s), 7.23(8H, s).

4-(4,4'-Dimethoxybenzhydryl)-1-piperazineethanol: Oil, IR(Neat): 3330 cm$^{-1}$. NMR(CDCl$_3$)δ:2.3–2.7(10H, m), 3.15(1H, broad, OH), 3.55(2H, t, J=6), 3.74(6H, s), 4.14(1H, s), 6.78(4H, d, J=9), 7.27(4H, d, J=9).

4-(4,4'-Dimethylbenzhydryl)-1-piperazineethanol: Oil, IR(Neat): 3400 cm$^{-1}$. NMR(CDCl$_3$)δ: 2.24(6H, s), 2.2–2.7(10H, m), 3.54(2H, t, J=6), 4.21(1H, s), 6.9–7.3(8H, m).

(2) To 4-benzhydryl-1-piperazineethanol (18.1 g) was added diketene (5.1 g) and the mixture was heated under stirring at 70°–80° C. for 1.5 hours. The product obtained was purified by silica gel chromatography [eluent: hexaneethyl acetate (3:2)] to give 2-(4-benzhydryl-1-piperazinyl)-ethyl acetoacetate as an oil. Yield 17.1 g (73.6%). IR(Neat): 1730, 1715 cm$^{-1}$. NMR(CDCl$_3$)δ: 2.22(3H, s), 2.43(10H, broad) 3.39(2H, s), 4.18(1H, s), 4.20(2H, t, J=6), 6.64–7.73(10H, m).

In the same manner as above, there were obtained the following compounds:

2-[4-(4,4'-Difluorobenzhydryl)-1-piperazinyl]ethyl acetoacetate: Oil, IR(Neat): 1740, 1715 cm$^{-1}$. NMR(CDCl$_3$)δ: 2.25(3H, s), 2.2–2.7(10H, m), 3.40(2H, s), 4.18(1H, s), 4.25(2H, t, J=6), 6.8–7.5(8H, m).

2-[4-(4,4'-Dichlorobenzhydryl)-1-piperazinyl]ethyl acetoacetate: Oil, IR(Neat): 1740, 1715 cm$^{-1}$. NMR(CDCl$_3$)δ: 2.23(3H, s), 2.3–2.8(10H, m), 3.42(2H, s), 4.17(1H, s), 4.23(2H, t, J=6), 7.28(8H, s).

2-[4-(4,4'-Dimethoxybenzhydryl)-1-piperazinyl]ethyl acetoacetate: Oil, IR(Neat): 1740, 1715 cm$^{-1}$. NMR(CDCl$_3$)δ: 2.23(3H, s), 2.3–2.8(10H, m), 3.40(2H, s), 3.73(6H, s), 4.13(1H, s), 4.24(2H, t, J=6), 6.77(4H, d, J=9), 7.31(4H, d, J=9).

2-[4-(4,4'-Dimethylbenzhydryl)-1-piperazinyl]acetoacetate: Oil, IR(Neat): 1740, 1715 cm$^{-1}$. NMR(CDCl$_3$)δ: 2.23(3H, s), 2.25(6H, s), 2.3–2.8(10H, m), 3.40(2H, s), 4.12(1H, s), 4.23(2H, t, J=6), 7.03(4H, d, J=9), 7.27(4H, d, J=9).

REFERENCE EXAMPLE 2

(1) To a mixture of 1-(4-fluorophenyl)piperazine (7.24 g), potassium carbonate powder (13.9 g) and N,N-dimethylformamide (30 ml) was added dropwise ethylene bromohydrin (10.0 g) under stirring. The mixture was stirred at room temperature for 3 hours, diluted with 100 ml of water and extracted with ethyl ether. The ethyl ether layer was washed with saturated aqueous sodium chloride and dried over anhydrous sodium sulfate. The solvent was distilled off and the residue was purified by silica gel chromatography [eluent: hexane-ethyl acetate (1:3)] to give 7.12 g (79.0%) of 4-(4-fluorophenyl)-1-piperazineethanol as an oil. IR(Neat): 3150 cm$^{-1}$. NMR (CDCl$_3$)δ: 2.47–2.80(6H, m), 2.97–3.20(4H, m), 3.10(1H, s), 3.65(2H, t, J=5.5), 6.71–7.13(4H, m).

In the same manner as above, there were obtained the following compounds:

4-(3-Chlorophenyl)-1-piperazineethanol: Oil, IR(Neat): 3380 cm$^{-1}$. NMR(CDCl$_3$)δ: 2.47–2.79(6H, m), 3.06–3.35(5H, m), 3.68(2H, t, J=5.5), 6.65–7.48(4H, m).

4-(2-Methoxyphenyl)-1-piperazineethanol: Colorless crystals, m.p. 71°–72° C. IR(Nujol): 3370 cm$^{-1}$. NMR (CDCl$_3$)δ: 2.47–2.82(6H, m), 2.97–3.22(4H, m), 3.65(2H, t, J=5.5), 3.82(3H, s), 6.87(4H, broad s).

4-(3-Trifluoromethylphenyl)-1-piperazineethanol: Oil, IR(Neat): 3375 cm$^{-1}$. NMR(CDCl$_3$)δ: 2.47–2.80(6H, m), 3.13–3.38(5H, m), 3.67(2H, t, J=5.5), 6.80–7.44(4H, m).

(2) The 4-phenyl-1-piperazineethanol compounds obtained in the above (1) were reacted with diketene in the same manner as Reference Example 1-(2), whereby the following compounds were obtained:

2-[4-(4-Fluorophenyl)-1-piperazinyl]ethyl acetoacetate: Oil, IR(Neat): 1740, 1715 cm$^{-1}$. NMR(CDCl$_3$)δ: 2.25(3H, s), 2.49–2.84(7H, m), 2.93–3.24(4H, m), 3.46(2H, s), 4.28(2H, t, J=5.5), 6.67–7.07(4H, m).

2-[4-(3-Chlorophenyl)-1-piperazinyl]ethyl acetoacetate: Oil, IR(Neat): 1740, 1715 cm$^{-1}$. NMR(CDCl$_3$)δ: 2.24(3H, s), 2.50–2.82(7H, m), 3.06–3.13(4H, m), 3.44(2H, s), 4.28(2H, t), 6.60–7.36(4H, m).

2-[4-(2-Methoxyphenyl)-1-piperazinyl]ethyl acetoacetate Oil, IR(Neat): 1740, 1710 cm$^{-1}$. NMR(CDCl$_3$)δ: 2.30(3H, s), 2.59–2.83(6H, m), 2.96–3.20(4H, m), 3.44(2H, s), 3.83(3H, s), 4.29(2H, t, J=6), 6.87(4H, broad s).

2-[4-(3-Trifluoromethylphenyl)-1-piperazinyl]ethyl acetoacetate: Oil, IR(Neat): 1735, 1715 cm$^{-1}$. NMR(CDCl$_3$)δ: 2.28(3H, s), 2.54–2.83(6H, m), 3.12–3.36(4H, m), 3.48(2H, s), 4.31(2H, t, J=6), 6.87–7.45(4H, m).

REFERENCE EXAMPLE 3

(1) To a mixture of homopiperazine (5.0 g), potassium carbonate powder (13.8 g) and N,N-dimethylformamide (80 ml) was added ethylene bromohydrin (6.3 g) and the mixture was stirred at room temperature for 12 hours. Then, benzhydryl bromide (12.4 g) was added and the whole mixture was further stirred at room temperature for 6 hours, diluted with water and extracted with ethyl ether. The ethyl ether layer was washed with water and dried over anhydrous magnesium sulfate. The solvent was distilled off and the oily residue was purified by silica gel chromatography [eluent: chloroform-methanol (20:1)] to give 4-benzhydrylhomopiperazine-1-ethanol as an oil (2.7 g, 17.4%). IR(Neat): 3400 cm$^{-1}$. NMR(CDCl$_3$)δ: 1.6–1.9(2H, m), 2.5–2.9(10H, m), 3.08(1H, s), 3.52(2H, t, J=6), 4.57(1H, s), 7.0–7.5(10H, m).

(2) 4-Benzhydrylhomopiperazine-1-ethanol (2.6 g) was reacted with diketene in the same manner as Reference Example 1-(2) to give 2-(4-benzhydrylhomopiperazin-1-yl)ethyl acetoacetate as an oil (2.7 g, 81.8%). IR(Neat): 1735, 1715 cm$^{-1}$. NMR(CDCl$_3$)δ: 1.6–1.9(2H, m), 2.26(3H, s), 2.5–2.9(10H, m), 3.40(2H, s), 4.20(2H, t, J=6), 4.57(1H, s), 7.1–7.5(10H, m).

REFERENCE EXAMPLE 4

(1) 1-Piperazineethanol was benzylated with benzyl bromide in the same manner as Reference Example 1-(1) to give 4-benzyl-1-piperazineethanol as an oil. Yield 80.8%. NMR(CDCl$_3$)δ: 2.42–2.65(10H, m), 3.33(1H, s), 3.49(2H, s), 3.59(2H, t, J=5), 7.23(5H, s).

(2) 4-Benzyl-1-piperazineethanol was reacted with diketene in the same manner as Reference Example 1-(2) to give 2-(4-benzyl-1-piperazinyl)ethyl acetoacetate as an oil. Yield 90.2%. NMR(CDCl$_3$)δ: 2.26(3H, s), 2.47(8H, s), 2.61(2H, t, J=6), 3.41(2H, s), 3.47(2H, s), 4.22(2H, t, J=6), 7.21(5H, s).

REFERENCE EXAMPLE 5

(1) To a mixture of 1-(2-pyridyl)piperazine (5 g), potassium carbonate powder (9 g) and N,N-dimethylformamide (30 ml) was added dropwise ethylene bromohydrin (5.74 g) under stirring. The mixture was stirred at room temperature for 6 hours, diluted with water (100 ml) and extracted with chloroform. The chloroform layer was washed with water and dried over anhydrous sodium sulfate. The solvent was distilled off and the residue was purified by silica gel chromatography [eluent: dichloromethane-methanol (95:5)] to give 4-(2-pyridyl)-1-piperazineethanol as crystals, m.p. 82.5°–84° C. Yield 4.68 g (73.7%).

(2) To a solution of 4-(2-pyridyl)-1-piperazineethanol (4.65 g) in toluene (3 ml) was added dropwise diketene (2.26 g) under stirring at 70°–80° C. The mixture was further stirred at room temperature for an hour and purified by silica gel chromatography [eluent: dichloromethanemethanol (95:5)] to give 2-[4-(2-pyridyl)-1-piperazinyl]ethyl acetoacetate as an oil (5.12 g, 78.3%). IR(Neat): 1740, 1715 cm$^{-1}$. NMR(CDCl$_3$)δ: 2.26(3H, s), 2.47–2.79(6H, m), 3.40–3.64(6H, m), 4.27(2H, t, J=6), 6.43–6.69(2H, m), 7.24–7.56(1H, m), 8.02–8.18(1H, m).

REFERENCE EXAMPLE 6

(1) 1-Piperazinepropanol was reacted with benzhydryl bromide in the same manner as Reference Example 1-(1) to give crystals of 4-benzhydryl-1-piperazinepropanol, m.p. 126°–128° C. Yield 76.3%.

(2) 4-Benzhydryl-1-piperazinepropanol was reacted with diketene in the same manner as Reference Example 2-(1) to give 3-(4-benzhydryl-1-piperazinyl)propyl acetoacetate as an oil. Yield 96.3%. NMR(CDCl$_3$)δ: 1.62–1.98(2H, m), 3.40(2H, s), 4.16(2H, t, J=6.8), 4.20(1H, s), 7.10–7.49(10H, m).

REFERENCE EXAMPLE 7

In the same manner as Reference Example 2-(1), there were obtained the following compounds:

4-(2-Chlorophenyl)-1-piperazineethanol: Oil. IR(Neat): 3380 cm$^{-1}$. NMR(CDCl$_3$)δ: 2.53–2.89(7H, m), 3.01–3.25(4H, m), 3.66(2H, t, J=5.4), 6.82–7.44(4H, m).

4-(4-Chlorophenyl)-1-piperazineethanol: M.p. 107°–108° C.

4-(2-Methylphenyl)-1-piperazineethanol: Oil 4-(4-Methoxyphenyl)-1-piperazineethanol: M.p. 87.5°–88° C.

4-Phenyl-1-piperazineethanol: M.p. 80°–81.5° C.

4-(3-Chloro-4-methylphenyl)-1-piperazineethanol: M.p. 91°–93° C.

4-(2,3-Dichlorophenyl)-1-piperazineethanol: Oil 4-(2,5-Dichlorophenyl)-1-piperazineethanol: Oil

REFERENCE EXAMPLE 8

In the same manner as Reference Example 1-(2), there were obtained the following compounds:

2-[4-(2-Chlorophenyl)-1-piperazinyl]ethyl acetoacetate: Oil

2-[4-(4-Chlorophenyl)-1-piperazinyl]ethyl acetoacetate: Oil

2-[4-(2-Methylphenyl)-1-piperazinyl]ethyl acetoacetate: Oil

2-[4-(4-Methoxyphenyl)-1-piperazinyl]ethyl acetoacetate: Oil 2-(4-Phenyl-1-piperazinyl)ethyl acetoacetate: Oil 2-[4-(3-Chloro-4-methylphenyl)-1-piperazinyl]ethyl acetoacetate: Oil 2-[4-(2,3-Dichlorophenyl)-1-piperazinyl]ethyl acetoacetate: Oil 2-[4-(2,5-Dichlorophenyl)-1-piperazinyl]ethyl acetoacetate: Oil

What is claimed is:

1. A dihydropyridine compound of the formula

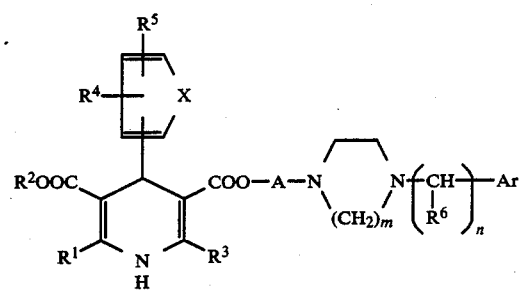

(I)

wherein $R^1$, $R^2$ and $R^3$ are the same or different and each is $C_{1-6}$-alkyl, $C_{3-6}$-cycloalkyl, $C_{3-6}$-cycloalkyl-$C_{1-6}$-alkyl, or $C_{3-7}$-alkoxyalkyl;

$R^4$ and $R^5$ are the same or different and each is hydrogen, halogen, nitro, trifluoromethyl, $C_{1-6}$-alkyl, $C_{3-6}$-cycloalkyl, $C_{1-3}$-alkoxy, cyano, $C_{2-4}$-alkoxycarbonyl or $C_{1-3}$-alkylthio; $R^6$ is hydrogen, $C_{1-6}$-alkyl, $C_{3-6}$-cycloalkyl, 2-pyridyl, 3-pyridyl, 4-pyridyl, phenyl-$C_{1-3}$-alkyl optionally substituted on the phenyl ring by halogen, nitro trifluoromethyl, $C_{1-6}$-alkyl, $C_{3-6}$-cycloalkyl, $C_{1-3}$-alkoxy, cyano, $C_{1-3}$-alkylthio and $C_{2-4}$-alkoxycarbonyl groups, or phenyl, or naphthyl, wherein the phenyl or naphthyl groups can be optionally substituted by one or two halogen, nitro, trifluormethyl, $C_{1-6}$-alkyl, $C_{3-6}$-cycloalkyl, $C_{1-3}$-alkoxy, cyano, $C_{1-3}$-alkylthio and $C_{2-4}$-alkoxycarbonyl groups; A is $C_{2-4}$-alkylene;

Ar is 2-pyridyl, 3-pyridyl, 4-pyridyl or phenyl or naphthyl which phenyl or naphthyl can be optionally substituted by one or two nitro, trifluoromethyl, halogen, $C_{1-6}$-alkyl, $C_{3-6}$-cycloalkyl, $C_{1-3}$-alkoxy, cyano, $C_{1-3}$-alkylthio and $C_{2-4}$-alkoxycarbonyl groups;

m is an integer of 1 to 3 inclusive;
n is an integer of 1 or 2, and
wherein

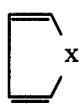

represents phenyl, 2-pyridyl, 3-pyridyl, 4-pyridyl, 2-furyl, 2-thienyl, 2,1,3-benzoxadiazol-4-yl, or 2,1,3-benzothiadiazol-4-yl; or a pharmaceutically acceptable salt thereof.

2. A dihydropyridine compound of the formula

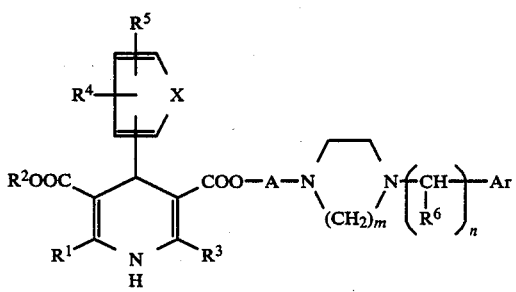

wherein $R^1$, $R^2$ and $R^3$ are the same or different and each is $C_{1-6}$-alkyl, $C_{3-6}$-cycloalkyl, $C_{3-6}$-cycloalkyl-$C_{1-6}$-alkyl, or $C_{3-7}$-alkoxyalkyl;

$R^4$ and $R^5$ are the same or different and each is hydrogen, halogen, nitro, trifluoromethyl, $C_{1-6}$-alkyl, $C_{3-6}$-cycloalkyl, $C_{1-3}$-alkoxy, cyano, $C_{2-4}$-alkoxycarbonyl or $C_{1-3}$-alkylthio;

$R^6$ is hydrogen, $C_{1-6}$-alkyl, $C_{3-6}$-cycloalkyl, 2-pyridyl, 3-pyridyl, 4-pyridyl, phenyl-$C_{1-3}$-alkyl optionally substituted on the phenyl ring by halogen, nitro trifluoromethyl, $C_{1-6}$-alkyl, $C_{3-6}$-cycloalkyl, $C_{1-3}$-alkoxy, cyano, $C_{1-3}$-alkylthio and $C_{2-4}$-alkoxycarbonyl groups, or naphthyl, wherein the phenyl or naphthyl groups can be optionally substituted by one or two halogen, nitro, trifluoromethyl, $C_{1-6}$-alkyl, $C_{3-6}$-cycloalkyl, $C_{1-3}$-alkoxy, cyano, $C_{1-3}$-alkylthio and $C_{2-4}$-alkoxycarbonyl groups;

A is $C_{2-4}$-alkylene;

Ar is 2-pyridyl, 3-pyridyl, 4-pyridyl or phenyl or naphthyl which phenyl or naphthyl can be optionally substituted by one or two nitro, trifluoromethyl, halogen, $C_{1-6}$-alkyl, $C_{3-6}$-cycloalkyl, $C_{1-3}$-alkoxy, cyano, $C_{1-3}$-alkylthio and $C_{2-4}$-alkoxycarbonyl;

m is 2, and n is 1 or 2;
wherein

represents phenyl, 2-pyridyl, 3-pyridyl, 4-pyridyl, 2-furyl, 2-thienyl, 2,1,3-benzoxadiazol-4-yl, or 2,1,3-benzothiadiazol-4-yl; or a pharmaceutically acceptable salt thereof.

3. A dihydropyridine compound claimed in claim 1, wherein A is ethylene.

4. A dihydropyridine compound claimed in claim 1, wherein X is vinylene.

5. A dihydropyridine compound claimed in claim 1, wherein Ar is phenyl.

6. A dihydropyridine compound claimed in claim 1, wherein X is azomethine.

7. A dihydropyridine compound claimed in claim 1, wherein X is oxygen.

8. A dihydropyridine compound claimed in claim 1, wherein $R^6$ and Ar each is a phenyl group and n is 1.

9. A dihydropyridine compound claimed in claim 1, wherein $R^6$ and Ar each is phenyl, X is vinylene, A is ethylene, m is 2, and n is 1.

10. A dihydropyridine compound claimed in claim 1, which is 2-(4-benzhydryl-1-piperazinyl)ethyl methyl 2,6-dimethyl-4-(3-nitrophenyl)-1,4-dihydropyridine-3,5-dicarboxylate.

11. A dihydropyridine compound claimed in claim 1, which is 2-[4-(4,4'-difluorobenzhydryl)-1-piperazinyl]ethyl methyl 2,6-dimethyl-4-(3-nitrophenyl)-1,4-dihydropyridine-3,5-dicarboxylate.

12. A dihydropyridine compound claimed in claim 1, which is 2-[4-(4,4'-dimethylbenzhydryl)-1-piperazinyl]ethyl methyl 2,6-dimethyl-4-(3-nitrophenyl)-1,4-dihydropyridine-3,5-dicarboxylate.

13. A dihydropyridine compound claimed in claim 1, which is 2-[4-(4,4'-dichlorobenzhydryl)-1-piperazinyl]ethyl methyl 2,6-dimethyl-4-(3-nitrophenyl)-1,4-dihydropyridine-3,5-dicarboxylate.

14. A dihydropyridine compound claimed in claim 1, which is 2-(4-benzhydryl-1-piperazinyl)ethyl methyl 4-(2,1,3-benzoxadiazol-4-yl)-2,6-dimethyl-1,4-dihydropyridine-3,5-dicarboxylate.

15. A pharmaceutical composition which comprises, as an active ingredient, an effective antihypertensive amount of a dihydropyridine compound or its salt as defined in claim 1, and a pharmaceutically acceptable carrier or diluent therefor.

* * * * *